(12) United States Patent
Slater et al.

(10) Patent No.: US 7,371,533 B2
(45) Date of Patent: May 13, 2008

(54) METHODS FOR SEPARATION OF POLYMERIC COMPOUNDS

(75) Inventors: Gary W. Slater, Ottawa (CA); Laurette C. McCormick, Chambly (CA); Annelise E Barron, Evanston, IL (US); Robert J. Meagher, Mountain House, CA (US)

(73) Assignees: University of Ottawa, Ottawa (CA); Northwestern University, Evanston, IL (US)

( * ) Notice: Subject to any disclaimer, the term of this patent is extended or adjusted under 35 U.S.C. 154(b) by 1 day.

(21) Appl. No.: 11/241,990

(22) Filed: Oct. 4, 2005

(65) Prior Publication Data

US 2006/0177840 A1   Aug. 10, 2006

Related U.S. Application Data

(60) Provisional application No. 60/615,600, filed on Oct. 5, 2004.

(51) Int. Cl.
*C12Q 1/68* (2006.01)
*C07H 21/02* (2006.01)
*C07H 21/04* (2006.01)

(52) U.S. Cl. .................... 435/6; 536/23.1; 536/24.3

(58) Field of Classification Search .................... 435/6; 536/23.1, 24.3
See application file for complete search history.

(56) References Cited

U.S. PATENT DOCUMENTS

2003/0088056 A1* 5/2003 Barron ........................ 530/324

OTHER PUBLICATIONS

Author(s): Ren, H., Karger, A.E., Oaks, F., Menchen, S., Slater, G.W., Drouin, G., Title: Separating DNA sequencing fragments without a sieving matrix Source: Electrophoresis Year; 1999 Chapter 20 pp. 2501-2509.
Author(s): Völkel, A.R., Noolandi, J. Title: Mobilities of Labeled and Unlabeled Single-Stranded DNA in Free Solution Electrophoresis Source: Macromolecules Year: 1995 Chapter 28 pp. 8182-8189.
Author(s): Mayer, P., Slater, G.W., Drouin, G. Title: Theory of DNA Sequencing Using Free-Solution Electrophoresis of Protein-DNA Complexes Source: Anal. Chem. Year: 1994 Chapter 66 pp. 1777-1780.
Author(s): Heller, C., Slater, G.W., Mayer, P., Dovichi, N., Pinto, D., Viovy, J.-L., Drouin, G., Title: Free-solution electrophoresis of DNA Source: J. Chrom. A. Year: 1998 Chapter 806 pp. 113-121.
Author(s): Desruisseaux, C., Long, D., Drouin, G., Slater, G.W. Title: Electrophoresis of Composite Molecular Objects. 1. Relation between Friction, Charge, and Ionic Strength in Free Solution Source: Macromolecules Year: 2001 Chapter 34 pp. 44-52.
Author(s); Desruisseaux, C., Drouin, G., Slater, G.W. Title; Electrophoresis of Composite Molecular Objects. 2. Competition between sieving and Frictional Effects in Polymer Solutions Source; Macromolecules Year: 2001 Chapter 34 pp. 5280-5286.
Author(s): Viovy, J.L. Title: Electrophoresis of DNA and other polyelectrolytes: Physical mechanisms Source: Rev. Mod. Phys. Year: 2000 Chapter 72 pp. 813-872.
Author(s): Olivera, B.M., Baine, P., Davidson, N. Title: Electrophoresis of the Nucleic Acids Source: Biopolymers Year: 1964 Chapter 2 pp. 245-257.
Author(s): Stellwagen, N.C., Gelfi, C., Righetti, P.G. Title: The Free Solution Mobility of DNA Source: Biopolymers Year: 1997 Chapter 42 pp. 687-703.
Author(s): Stellwagen, N.C., Stellwagen, E. Title: The free solution mobility of DNA in Tris-acetate-EDTA buffers of different concentrations, with and without added NaCl Source: Electrophoresis Year: 2002 Chapter 23 pp. 1935-1941.
Author(s): Vreeland, W.N., Desruisseaux, C., Karger, A.E., Drouin, G., Slater, G.W., Barron, A.E. Title: Molar Mass Profiling of Synthetic Polymers by Free-Solution Capillary Electrophoresis of DNA-Polymer Conjugates Source: Anal. Chem. Year: 2001 Chapter 73 pp. 1795-1803.
Author(s): Vreeland, W.N., Slater, G.W., Barron, A.E. Title: Profiling Solid-Phase Synthesis Products by Free-Solution Conjugate Capillary Electrophoresis Source: Bioconj. Chem. Year: 2002 Chapter 13 pp. 663-670.
Author(s): McCormick, L.C., Slater, G.W., Karger, A.E., Vreeland, W.N., Barron, A.E., Desruisseaux, C., Drouin, G. Title: Capillary electrophoretic separation of uncharged polymers using polyelectrolyte engines Source: Electrophoresis Year: 2001 Chapter 924 pp. 43-52.

(Continued)

*Primary Examiner*—Ethan Whisenant
(74) *Attorney, Agent, or Firm*—Osler, Hoskin & Harcourt LLP

(57) ABSTRACT

Recently two techniques using free solution electrophoresis to separate charged-uncharged polymer conjugates have proven successful: End Labeled Free Solution Electrophoresis (ELFSE) for DNA sequencing, and Free Solution Conjugate Electrophoresis (FSCE) for molar mass profiling of uncharged polymers. Previous attempts have been made to analyze experimental data generated by these new techniques for the electrophoresis of molecules with varying charge distributions. However, the importance of the ends of the polymers in determining the polymer's overall mobility was neglected in previous work. Through a careful investigation and a reanalysis of the experimental data, it is determined here that this "end effect" critically impacts the behavior of polymers and charged-uncharged polymer conjugates during electrophoresis. In this way, the invention provides for methods that exploit this "end effect" for the separation of polymeric molecules on the basis of size, including for example DNA separation and sequencing techniques.

20 Claims, 15 Drawing Sheets

OTHER PUBLICATIONS

Author(s): Long, D. Dobrynin, A.V., Rubinstein, M., Ajdari, A., Title: Electrophoresis of polyampholytes Source: J. Chem. Phys. Year: 1998 Chapter 108 pp. 1234-1244.

Author(s): Won, J.-I., Meagher, R.J., Barron, A.E. Title: Characterization of Glutamine Deamidation in a Long, Repetitive Protein Polymer via Bioconjugate Capillary Electrophoresis Source: Biomacromolecules Year: 2004 Chapter 5 pp. 618-627.

Author(s): Noolandi, J. Title: A New Concept for Sequencing DNA by Capillary Electrophoresis Source: Electrophoresis Year: 1992 Chapter 13 pp. 394-395.

Author(s): Meagher, R.J. Won, J.I., McCormick, L.C. Nedelcu, S., Bertrand, M. M. Title: End-labeled free-solution electrophoresis of DNA Source: Electrophoresis Year: 2005 Chapter 26 pp. 331-350.

Author(s): Bullock, J. Source: J. Chrom. Year: 1993 Chapter 645 pp. 169-177.

Author(s): Zuckermann, R. N., Kerr, J. M., Kent, S. B. H., Moos, W. H.. Title: Efficient Method For the Preparation of Peptoids [Oligo(N-Substituted Glycines)] By Submonomer Solid-Phase Synthesis Source: J. Am. Chem. Soc. Year: 1992 Chapter 114 pp. 10646-10647.

Author(s): Vreeland, W. N., Barron, A. E. Title: Free-solution capillary electrophoresis of polypeptoid- oligonucleotide conjugates Source: Abstracts of Papers of the American Chemical Society Year: 2000 Chapter 219 pp. 555-556.

Author(s): Vreeland, W.N., Meagher, R. J., Barron, A. E. Title: Multiplexed, High-Throughput Genotyping by Single-Base Extension and End-Labeled Free-Solution Electrophoresis Source: Anal. Chem. Year: 2002 Chapter 74 pp. 4328-4333.

Author(s): Haynes, R. D., Meagher, R.J., Won, J. I., Bogdan, F. M. Barron, A. E. Title: Comb-like, monodisperse polypeptoid drag-tags for DNA separation by End-Labeled Free-Solution Electrophoresis (ELFSE) Source: Bioconjugate Chem. Year: 2005 Chapter 16 pp. 929-938.

Author(s): Won, J. I., Barron, A. E. Title: A new cloning method for preparation of long repetitive polypeptides without sequence requirement Source: Macromolecules Year: 2002 Chapter 35 pp. 8281-8287.

Author(s): Won, J. I. Meagher, R. J., Barron, A. E. Title: Protein polymer drag-tags for DNA separations by end-labeled free-solution electrophoresis Source: Electrophoresis Year: 2005 Chapter 26 pp. 2138-2148.

Author(s): Doherty, E. A. S., Berglund, K. D., Buchholz, B. A., Kourkine, I. V., Przybycien, T.M. Title: Critical factors for high-performance physically adsorbed (dynamic) polymeric wall coatings for capillary electrophoresis of DNA Source: Electrophoresis Year: 2002 Chapter 23 pp. 2766-2776.

Author(s): McCormick, L. C., Slater, G. W., Karger, A. E., Vreeland, W. N., Barron, A. E. Title: Capillary electrophoretic separation of uncharged polymers using polyelectrolyte engines—Theoretical model Source: J. Chromatogr. A Year: 2001 Chapter 924 pp. 43-52.

Author(s): Haynes, R. D., Meagher, R. J., Coyne, J. Barron, A. E. Title: Comb-like poly-N-substituted glycines as end-labeled free-solution electrophoresis (ELFSE) drag-tags for DNA sequencing Source: Abstracts of the Papers of the American Chemical Society Year: 2006 Chapter 231 pp. 131-ORGN, 26.

Author(s): Meagher, R. J., McCormick, L. C., Haynes, R. D., Won, J. I., Lin, J. S., Slater, G. W., Barron, A. E. Title: Free-solution electrophoresis of DNA modified with drag-tags at both ends Source: Electrophoresis Year 2006 Chapter 27 pp. 1702-1712.

Author(s): McCormick, L. C., Slater, G. W. Title: A theroetical study of the possible use of electroosmotic flow to extend the read length of DNA sequencing by end-labeled free solution electrophoresis Source: Electrophoresis Year: 2006 Chapter 27 pp. 1693-1701.

Author(s): Nedelcu, S., Slater, G. W. Title: Branched polymeric labels used as drag-tags in free-solution electrophoresis of ssDNA Source: Electrophoresis Year: 2005 Chapter 26 pp. 4003-4015.

Author(s): McCormick, L. C., Slater, G. W. Title: The molecular end effect and its critical impact on the behavior of charged-uncharged polymer conjugates during free-solution electrophoresis Source: Electrophoresis Year: 2005 Chapter 26 pp. 1659-1667.

Author(s): Völkel, A. R., Noolandi, J. Title: Mobilities of Labeled and Unlabeled Single-Stranded DNA in Free Solution Electrophoresis Source: Macromolecules Year: 1995 Chapter 28 pp. 8182-8189.

Author(s): Noolandi, J. Title: A new concept for separating nucleic acid by electrophoresis in solution using hybrid synthetic end labelled-nucleic acid molecules Source: Electrophoresis Year: 1993 Chapter 14 pp. 680-681.

Author(s): Stefansson, M., Novotny, M. Title: Separation of Complex Oligosaccharide Mixtures by Capillary Electrophoresis in the Open-Tubular Format Source: Anal. Chem. Year: 994 Chapter 66 pp. 3466-3471.

Author(s): Sudor, J., Novotny, M. V. Title: End-Label, Free-Solution Capillary Electrophoresis of Highly Charged Oligosaccharides Source: Anal. Chem. Year: 1995 Chapter 67 pp. 4205-4209.

Author(s): Sudor, J., Novotny, M. V. Title: End-Label Free-Solution Electrophoresis of the Low Molecular Weight Heparins Source: Anal. Chem. Year: 1997 Chapter 69 pp. 3199-3204.

Author(s): Carlsson, C., Jonsson, M., Norden, B., Dulay, M. T., Zare, R. N., Noolandi, J., Nielsen, P.E., Tsui, L. C., Zielenski, J. Title: Screening for genetic mutations Source: Nature Year: 1996 Chapter 380 pp. 207.

Author(s): Long, D., Viovy, J-L., Ajdari, A. Title: Simultaneous Action of Electric Fields and Nonelectric Forces on a Polyelectrolyte: Motion and Deformation Source: The American Physical Society Year: 1996 vol. 76 No. 20 pp. 3858-3861.

Author(s): Long, D., Viovy, J-L., Ajdari, A. Title: A Zimm model for polyelectrolytes in an electric field Source: J. Phys. Year: 1996 Matter 8 pp. 9471-9475.

Author(s): Long, D., Ajdari, A. Title: Electrophoretic mobility of composite objects in free solution: Application to DNA separation Source: Electrophoresis Year: 1996 Chapter 17 pp. 1161-1166.

Author(s): Long, D., Viovy, J-L., Ajdari, A. Title: Stretching DNA with Electric Fields Revisited Source: Biopolymers Year: 1996 vol. 39 pp. 755-759.

Author(s): Meagher, R. J., Seong, J., Laaibinis, P. E., Barron, A. E. Title: A very thin coating for capillary zone electrophoresis of proteins based on a tri(ethylene glycol)-terminated alkyltrichlorosilane Source: Electrophoresis Year: 2004 Chapter 25 pp. 405-414.

Author(s): Vreeland, W. N., Williams, S. J., Barron, A. E., Sassi, A. P. Title: Tandem Isotachophoresis-Zone Electrophoresis via Base-Mediated Destacking for Increased Detection Sensitivity in Microfluidic Systems Source: Anal. Chem. Year: 2003 Chapter 75 pp. 3059-3065.

Author(s): Vreeland, W. N., Slater, G. W., Barron, A. E. Title: Profiling Solid-Phase Synthesis Products by Free-Solution Conjugate Capillary Electrophoresis Source: Bioconjugate Chemistry Year: 2002 Chapter 13(3) pp. 663-670.

Vreeland Wyatt N and Barron Annelise E., "Free-Solution Capillary Electrophoresis of Polypeptoid-Oligonucleotide Conjugates", American Chemical Society, Polymer Preprints, 2000, 41 (1), pp. 1018-1019, USA.

* cited by examiner

| Drag-tag | Structure |
|---|---|
| NMEG-20<br>NMEG-40<br>NMEG-44 | 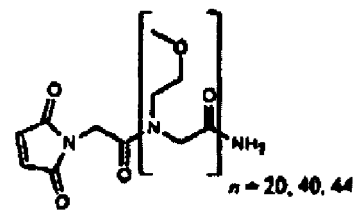 |
| Branched<br>NMEG-70 | |
| P1-169 | H₂N - (Gly Ala Gly Gln Gly Ser Ala)₂₄ Gly - COOH |
| P2-127 | H₂N-(GAGTGSA)₄-GAGTGRA-(GAGTGSA)₇-<br>GAGTGRA-(GAGTGSA)₅-G-COOH |

Fig. 9

```
┌─────────────────────────────────┐
│  Synthesizing a first plurality of
│  ssDNA molecules each comprising a
│  sequence identical to at least a       ─── 200
│  portion at or near the 5' end of a
│  section of DNA, each corresponding
│  to a specific nucleotide
└─────────────────────────────────┘
                │
                ▼
┌─────────────────────────────────┐
│  Attaching a chemical moiety            ─── 201
│  at or near each end of the
│  ssDNAs
└─────────────────────────────────┘
                │
                ▼
┌─────────────────────────────────┐
│  Subjecting the doubly end              ─── 202
│  labeled ssDNAs to free-
│  solution electrophoresis
└─────────────────────────────────┘
                │
                ▼
┌─────────────────────────────────┐
│  Identifying the nucleotide             ─── 203
│  sequence
└─────────────────────────────────┘
```

Fig. 15

SEQUENCE LISTING

<160> NUMBER OF SEQ ID NOS: 11

<210> SEQ ID NO 1
<211> LENGTH: 20
<212> TYPE: DNA
<213> ORGANISM: Artificial sequence
<220> FEATURE:
<223> OTHER INFORMATION: T20-dithiol, produced by chemical synthesis
<220> FEATURE:
<221> NAME/KEY: misc_feature
<222> LOCATION: (1)..(1)
<223> OTHER INFORMATION: n = t with 5'-thiol linker with 6-carbon spacer
<220> FEATURE:
<221> NAME/KEY: misc_feature
<222> LOCATION: (10)..(10)
<223> OTHER INFORMATION: n = internal fluorescein-dT base
<220> FEATURE:
<221> NAME/KEY: misc_feature
<222> LOCATION: (20)..(20)
<223> OTHER INFORMATION: n = t with 3'-thiol linker with 3 carbon spacer

<400> SEQUENCE: 1
nttttttttn ttttttttn                                                  20

<210> SEQ ID NO 2
<211> LENGTH: 40
<212> TYPE: DNA
<213> ORGANISM: Artificial sequence
<220> FEATURE:
<223> OTHER INFORMATION: T40-dithiol, produced by chemical synthesis
<220> FEATURE:
<221> NAME/KEY: misc_feature
<222> LOCATION: (1)..(1)
<223> OTHER INFORMATION: n = t with 5'-thiol linker with 6-carbon spacer
<220> FEATURE:
<221> NAME/KEY: misc_feature
<222> LOCATION: (20)..(20)
<223> OTHER INFORMATION: n = internal fluoresein-dT base
<220> FEATURE:
<221> NAME/KEY: misc_feature
<222> LOCATION: (40)..(40)
<223> OTHER INFORMATION: n = t with 3'-thiol linker with 3-carbon spacer

<400> SEQUENCE: 2
nttttttttt ttttttttn tttttttttt ttttttttn                             40

<210> SEQ ID NO 3
<211> LENGTH: 30
<212> TYPE: DNA
<213> ORGANISM: Artificial Sequence
<220> FEATURE:
<223> OTHER INFORMATION: M13-forward, produced by chemical synthesis
<220> FEATURE:
<221> NAME/KEY: misc_feature
<222> LOCATION: (1)..(1)
<223> OTHER INFORMATION: n = c with 5'thiol linker with 6-carbon spacer
<220> FEATURE:
<221> NAME/KEY: misc_feature
<222> LOCATION: (3)..(3)
<223> OTHER INFORMATION: n = internal fluorescein dT base

<400> SEQUENCE: 3
ncntttaggg ttttcccagt cacgacgttg                                      30

<210> SEQ ID NO 4
<211> LENGTH: 20
<212> TYPE: DNA
<213> ORGANISM: Artificial Sequence
<220> FEATURE:
<223> OTHER INFORMATION: 75-reverse, produced by chemical synthesis

<400> SEQUENCE: 4
gagtcgacct gcaggcatgc                                          20

<210> SEQ ID NO 5
<211> LENGTH: 20
<212> TYPE: DNA
<213> ORGANISM: Artificial sequence
<220> FEATURE:
<223> OTHER INFORMATION: 75 Reverse-T, produced by chemical synthesis
<220> FEATURE:
<221> NAME/KEY: misc_feature
<222> LOCATION: (1)..(1)
<223> OTHER INFORMATION: n = g with 5'-thiol linker with 6-carbon spacer

<400> SEQUENCE: 5
nagtcgacct gcaggcatgc                                          20

<210> SEQ ID NO 6
<211> LENGTH: 20
<212> TYPE: DNA
<213> ORGANISM: Artificial sequence
<220> FEATURE:
<223> OTHER INFORMATION: 100 Reverse, produced by chemical synthesis

<400> SEQUENCE: 6
gagctcggta cccgggatc                                          20

<210> SEQ ID NO 7
<211> LENGTH: 20
<212> TYPE: DNA
<213> ORGANISM: Artificial Sequence
<220> FEATURE:
<223> OTHER INFORMATION: 100 Reverse-T, produced by chemical synthesis
<220> FEATURE:
<221> NAME/KEY: misc_feature
<222> LOCATION: (1)..(1)
<223> OTHER INFORMATION: n = g with 5'-thiol linker with 6-carbon spacer

<400> SEQUENCE: 7
nagctcggta cccgggatc                                          20

<210> SEQ ID NO 8
<211> LENGTH: 20
<212> TYPE: DNA
<213> ORGANISM: Artificial sequence
<220> FEATURE:
<223> OTHER INFORMATION: 150 Reverse, produced by chemical synthesis

<400> SEQUENCE: 8
gcggataaca atttcacaca                                          20

<210> SEQ ID NO 9
<211> LENGTH: 20
<212> TYPE: DNA
<213> ORGANISM: Artificial sequence
<220> FEATURE:
<223> OTHER INFORMATION: 150 Reverse-T, produced by chemical synthesis
<220> FEATURE:
<221> NAME/KEY: misc_feature
<222> LOCATION: (1)..(1)
<223> OTHER INFORMATION: n = g with 5'-thiol linker with 6-carbon spacer

<400> SEQUENCE: 9
ncggataaca atttcacaca                                          20

<210> SEQ ID NO 10

```
<211> LENGTH: 20
<212> TYPE: DNA
<213> ORGANISM: Artificial sequence
<220> FEATURE:
<223> OTHER INFORMATION: 200 Reverse, produced by chemical synthesis

<400> SEQUENCE: 10
ccaggcttta cactttatgc                                              20

<210> SEQ ID NO 11
<211> LENGTH: 20
<212> TYPE: DNA
<213> ORGANISM: Artificial sequence
<220> FEATURE:
<223> OTHER INFORMATION: 200 Reverse-T, produced by chemical synthesis
<220> FEATURE:
<221> NAME/KEY: misc_feature
<222> LOCATION: (1)..(1)
<223> OTHER INFORMATION: n = c with 5'-thiol linker with 6-carbon spacer

<400> SEQUENCE: 11
ncaggcttta cactttatgc                                              20
```

METHODS FOR SEPARATION OF POLYMERIC COMPOUNDS

CROSS REFERENCE TO RELATED APPLICATION

This application claims the priority right of prior U.S. patent application 60/615,600 filed on Oct. 5, 2004 by applicants herein.

GOVERNMENT INTERESTS

This invention was made in part with U.S. Government support under NIH Grant No. HG002918 and DOE Grant No. DE-FG02-99ER62789. The U.S. Government may retain certain rights in this invention.

FIELD OF THE INVENTION

The present invention relates to the field of polymer separation by electrophoresis, in particular the separation of charged polymers by electrophoresis. In particular, the invention relates to the field of separating polymers on the basis of size such as for example polynucleotides.

BACKGROUND TO THE INVENTION

In several areas of technology it is desirable to separate polymeric compounds on the basis of their size, configuration, charge or other fundamental characteristics. For example, techniques relating to molecular biology and biotechnology frequently involve the analysis of a mixture of polypeptides or polynucleotides, which may be separated in accordance with their relative sizes. Results can provide indication of the size and relative abundance of compounds in the mixture with significant accuracy. Indeed, some techniques enable the separation of polynucleotides with a resolution of a single nucleotide, which is critical for analysis such as DNA sequencing.

Traditionally, compounds such as polypeptides and polynucleotides are separated by electrophoresis involving the application of an electric current through a buffered solution containing the compounds. During the electrophoresis the compounds may be forced to migrate through a matrix material that hinders progression of the migration. Such matrix materials may include agarose or polyacrylamide. Longer polymeric compounds migrate more slowly through the matrix when compared to shorter polymeric compounds, resulting in fairly rapid separation of the compounds on the basis of polymer length.

More recently, much attention has been focused on the free-solution electrophoresis of charged-uncharged polymer conjugates in microchannel electrophoresis systems such as capillary electrophoresis or microchip electrophoresis systems. The performance of electrophoresis in free solution overcomes the need for gels or entangled polymer solutions for the electrophoretic separation of polyelectrolytes, while offering a means for the molar mass profiling of uncharged polymers. End-labeled free-solution electrophoresis (ELFSE), for instance, was successfully used to sequence ssDNA up to 110 bases in less than 20 minutes [1]. This technique cleverly uses an uncharged "label" or "drag" molecule attached to each single-stranded DNA (ssDNA) chain in order to break the local balancing between friction and electric force [2, 3, 4, 5, 6] which normally leads to co-migration of all ssDNA lengths [7, 8] (excepting very small fragments [9, 10]) in free solution. More recently, a complementary technique called free solution conjugate electrophoresis (FSCE) has been used to characterize uncharged, water-soluble polymers that can be uniquely conjugated to ssDNA [11, 12, 13]. Here the ssDNA chains are of uniform length, and act as engines to pull the varying lengths of uncharged polymers for electrophoresis leading to single-monomer resolution over a wide range of molecular sizes. In fact, the resolution obtained was approximately five times higher, and the separation efficiencies were increased by 150% compared to the more traditional RP-HPLC [12]. For both FSCE and ELFSE, the theoretical equation utilized for the overall mobility μ of the charged-uncharged block copolymer was a uniformly weighted average [5, 6. 11, 13]:

$$\mu = \mu_0 \frac{M_c}{N} = \mu_0 \frac{M_c}{M_c + \alpha_1 M_u} \quad (1)$$

where $M_c$ is the number of charged monomers each of mobility $\mu_c$, and $M_u$ is the number of uncharged monomers. This equation comes from a pioneer investigation of Long and co-workers into the electrophoresis of polymers containing both charged and uncharged monomers [14]. The factor $\alpha_1$ rescales $M_u$ account for the difference in hydrodynamic properties arising for example from the different persistence lengths (a measure of flexibility) of the charged and uncharged polymers. Hence the $\alpha_1$ value depends on the chemistry of the molecules and varies with both temperature and buffer ionic strength (which affect the molecules' flexibilities). In fact, $\alpha = \alpha_1 M_u$ enables a counting of uncharged units which have the same friction as one ssDNA monomer, such that the total number of effective monomers is $N = M_c + \alpha_1 M_u$. The $\alpha_1$ value is an important determinant of the mobility since the frictional drag of the uncharged polymer is what selectively slows down longer conjugates in FSCE, and determines the read length of ELFSE.

Therefore, it is generally known in the art that the modification of polynucleotides for example by the covalent attachment of selected moieties can increase the frictional 'drag' of the polynucleotide during free-solution electrophoresis.

The work of Long and coworkers, as well as the work of others, has increased our general understanding of the mechanisms of polymeric compound separation by free solution electrophoresis. Moreover, the use of tags to alter the frictional drag characteristics of oligonucleotides during free-solution electrophoresis has provided improvements in these techniques. Nonetheless, there remains a continuing need to develop methods for the separation of polymeric compounds that are simple, effective, and rapid. In particular there is a need to develop methods for the separation of polymeric compounds such as polypeptides or polynucleotides with a high level of accuracy and a resolution of a single amino acid or nucleotide.

SUMMARY OF THE INVENTION

It is an object of the present invention, at least in preferred embodiments, to provide a method for the separation of polymeric compounds.

It is another object of the present invention, at least in preferred embodiments, to provide a method for the separation of polymeric compounds with a resolution that permits differentiation of compounds that vary in size by only a few polymer units, or at least in more preferred embodiments, by a single polymer unit.

It is another object of the present invention, at least in preferred embodiments, to provide a method of separating polymeric compounds that takes advantage of the use of tags or covalently attached moieties to alter the frictional drag characteristics of the polymeric compound.

In one aspect of the present invention there is provided as method for separating polymeric compounds according to their relative lengths, the method comprising the steps of:

attaching a chemical moiety at or near each end of each of said linear polymeric compounds to generate double end labeled polymeric compounds; and subjecting the doubly end-labeled polymeric compounds to free-solution electrophoresis, each chemical moiety suitable to impart increased hydrodynamic friction to each end of each double end labeled polymeric compound thereby to facilitate separation of the double end labeled polymeric compounds according to their electrophoretic mobility during said free-solution electrophoresis. Preferably, the polymeric compounds are linear polymeric compounds. Preferably, the polymeric compounds are charged polymeric compounds. Preferably, the chemical moieties are uncharged (or slightly charged) chemical moieties. Preferably, the polymeric compounds are selected from polypeptides or polynucleotides. Preferably, the polymeric compounds are selected from, proteins, ssDNA, dsDNA and RNA.

In selected aspects, the chemical moieties are selected from polypeptides, and polypeptoids (i.e., poly-N-substituted glycines). In other aspects, the chemical moieties are selected from the group consisting of the protein Streptavidin, or a derivative thereof, N-methoxyethylglycine (NMEG) oligomers of length up to 300 monomer units (preferably up to 100 monomer units), and a molecule consisting of a poly(NMEG) backbone optionally with oligo (NMEG) branches.

In another aspect of the invention there is provided a method comprising the steps of:

(a) synthesizing a first plurality of ssDNA molecules each comprising a sequence identical to at least a portion at or near the 5' end of said section of DNA, said ssDNA molecules having substantially identical 5' ends but having variable lengths, the length of each ssDNA molecule corresponding to a specific adenine base in said section of DNA;

(b) synthesizing a second plurality of ssDNA molecules each comprising a sequence identical to at least a portion at or near the 5' end of said section of DNA, said ssDNA molecules having substantially identical 5' ends but having variable lengths, the length of each ssDNA molecule corresponding to a specific cytosine base in said section of DNA;

(c) synthesizing a third plurality of ssDNA molecules each comprising a sequence identical to at least a portion at or near the 5'end of said section of DNA, said ssDNA molecules having substantially identical 5' ends but having variable lengths, the length of each ssDNA molecule corresponding to a specific guanine base in said section of DNA;

(d) synthesizing a fourth plurality of ssDNA molecules each comprising a sequence identical to at least a portion at or near the 5'end of said section of DNA, said ssDNA molecules having substantially identical 5' ends but having variable lengths, the length of each ssDNA molecule corresponding to a specific thymine base in said section of DNA;

(e) attaching a chemical moiety to end nucleotides at or near each end of said ssDNA molecules to generate double-end labeled polymeric compounds; and (f) subjecting each plurality of ssDNA molecules to free solution electrophoresis; and (g) identifying the nucleotide sequence of the section of DNA in accordance with the relative electrophoretic mobilities of the ssDNAs in each plurality of ssDNAs;

wherein any of steps (a), (b), (c), and (d) may be performed in any order or simultaneously; and whereby each chemical moiety imparts increased hydrodynamic friction to each end of each double end labeled polymeric compound thereby to facilitate separation of the double end labeled polymeric compounds according to their resulting electrophoretic mobility.

Preferably, the chemical moieties are uncharged chemical moieties. Alternatively, in other preferred aspects the chemical moieties are selected from among polypeptides, and polypeptoids. Preferably, the chemical moieties are selected from the group consisting of Streptavidin, or a derivative thereof, N-methoxyethylglycine (NMEG) oligomers comprising up to 300 (preferably up to 100) monomer units, and a molecule consisting of a poly(NMEG) backbone optionally with oligo (NMEG) branches.

Preferably, the section of DNA comprises less than 2000 nucleotides. More preferably, the section of DNA comprises less than 1000 nucleotides. More preferably, the section of DNA comprises less than 500 nucleotides. More preferably, the section of DNA comprises less than 300 nucleotides. More preferably, the section of DNA comprises less than 100 nucleotides.

In another aspect the invention provides for a method for separating polymeric compounds according to their relative size, the method comprising the steps of:

attaching a chemical moiety to each end of the polymeric compounds; and subjecting the polymeric compounds to free solution electrophoresis.

Preferably, the difference in relative size of the polymeric compounds is a single polymer unit.

Preferably, the polymeric compounds comprise DNA, and each polymer unit is a nucleotide.

for FSCE with an $M_c=20$ ssDNA base engine plotted as a function of the number $M_u$ of monomers of PEG ($\alpha_1=0.138$). The solid curve is the case with the end effect taken into account, the dotted line would be expected were there no end effect. The lines cross at $M_u=140$ PEG monomers in this example.

Figure 4:
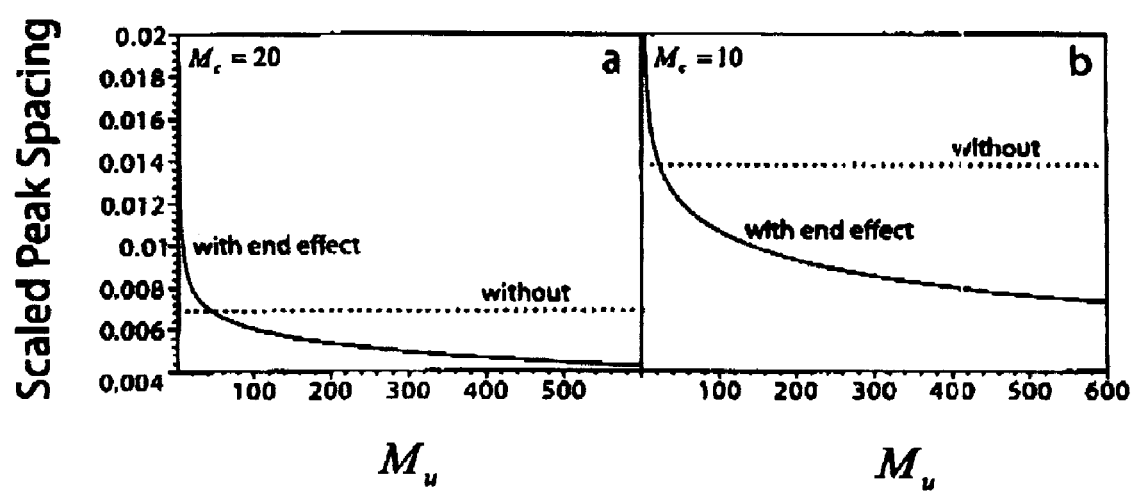

FIG. 4: Predicted peak sparing (scaled by the constant $$\left(\text{scaled by the constant } \frac{L}{\mu_0 E}\right)$$

for FSCE with a) an $M_c$=20 ssDNA base engine, and b) an $M_c$=10 ssDNA base engine, as a function of the number $M_u$ of monomers of PEG ($\alpha_1$=0.138). The solid curve is for the case with the end effect taken into account, the dotted line would be expected were there no end effect.

Figure 5:
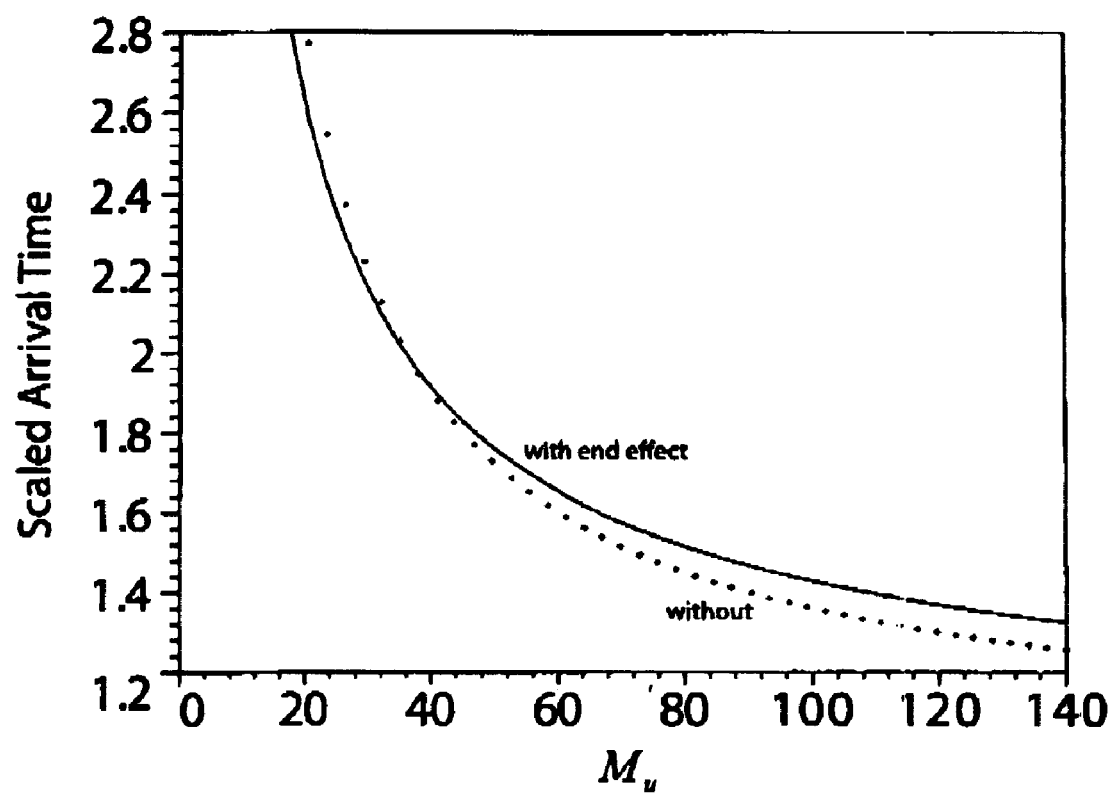

FIG. 5: Predicted arrival time at the detector for ELFSE, scaled by the constant $$\frac{L}{\mu_0 E},$$

as a function of the number $M_u$ of uncharged monomers. The uncharged drag molecule is of effective total size $\alpha=\alpha_1 M_u=36$. The solid line represents the case with the end effect taken into account, the dotted line would be expected were there no end effect.

Figure 6:
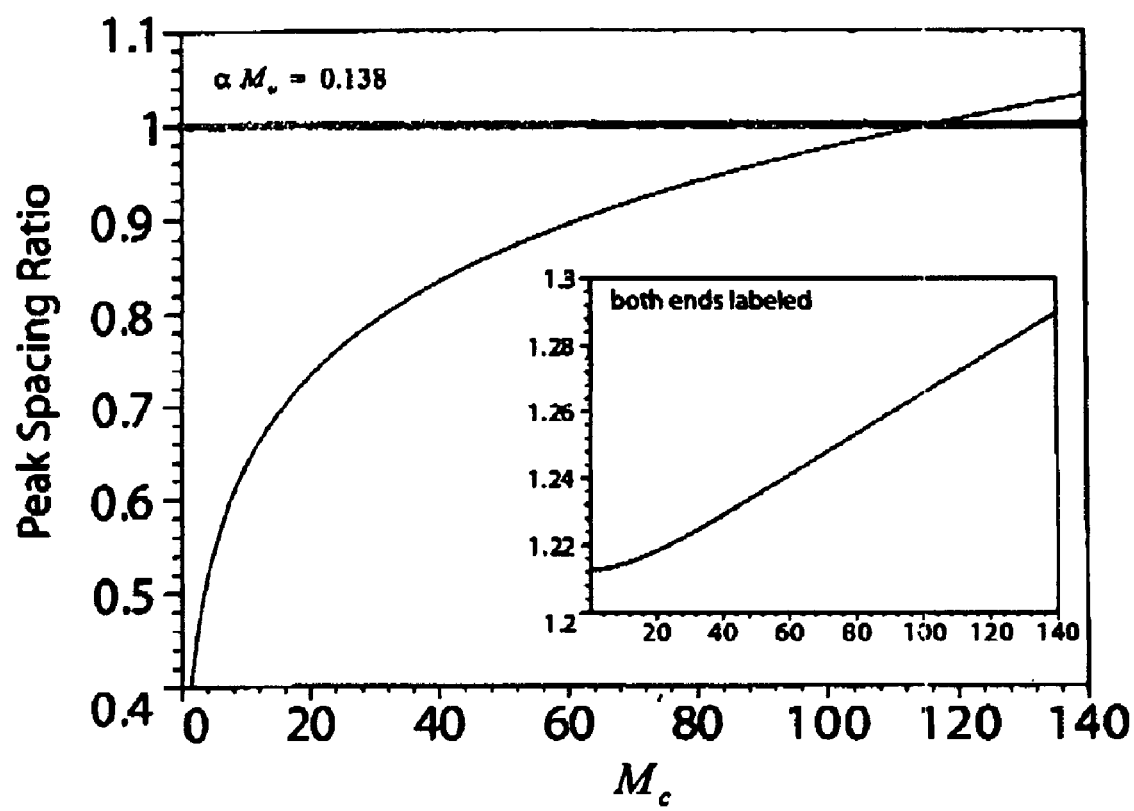

FIG. 6: Predicted ratio of ELFSE peak spacing with the end effect to that expected without, for an uncharged drag molecule of effective total size $\alpha=\alpha_1 M_u=36$ as used in [5, 6], as a function of the number $M_c$ of charged monomers. Inset: predicted ratio of ELFSE peak spacing with the end effect to that expected without, for an uncharged drag molecule of effective total size $\alpha=\alpha_1 M_u=36$ attached at both ends of the ssDNA as a function of the number $M_c$ of charged monomers.

Figure 7:
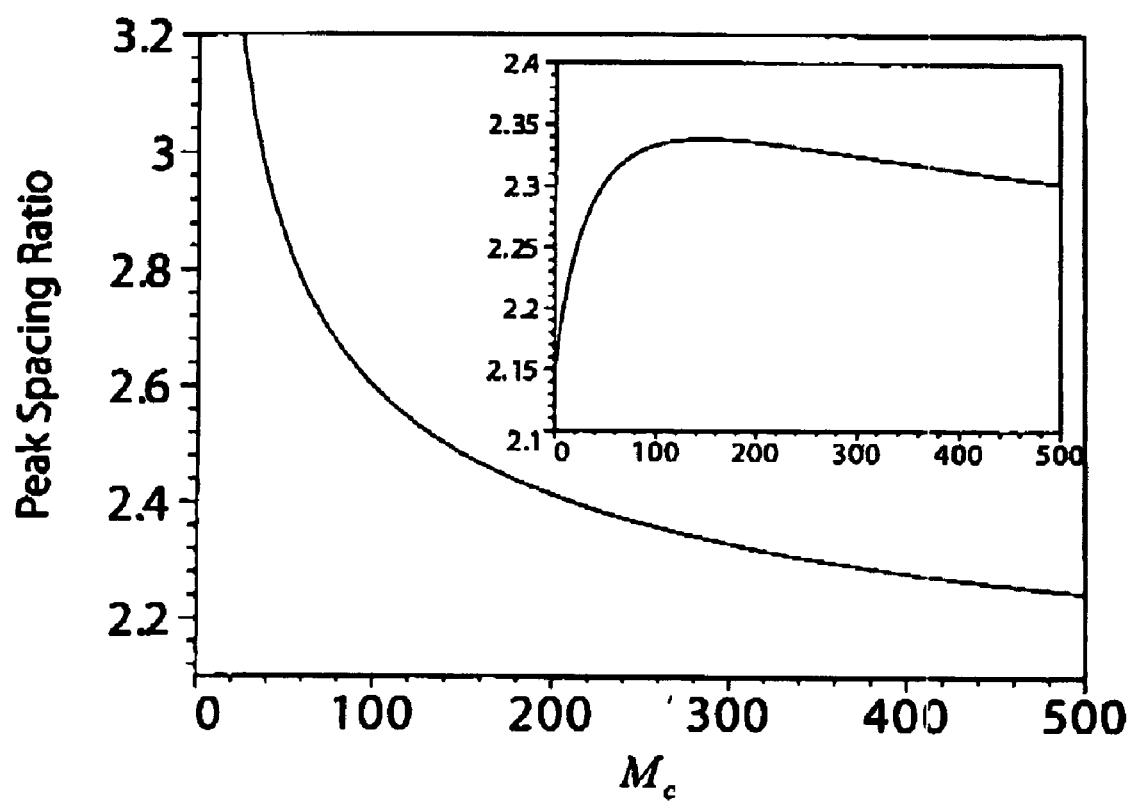

FIG. 7: Predicted ratio of ELFSE peak spacing for both ends of the ssDNA chain labeled with a drag of effective total size $\alpha=\alpha_1 M_u=36$ to that with only one end labeled. Inset: predicted ratio of ELFSE peak spacing, taking into account the end effect, for a hypothetical uncharged drag molecule of effective total size $\alpha=\alpha_1 M_u=100$ to that of effective total size $\alpha=\alpha_1 M_u=36$, showing the higher peak spacing of the larger drag molecule. Both curves were calculated by taking into account the end effect.

Figure 8:
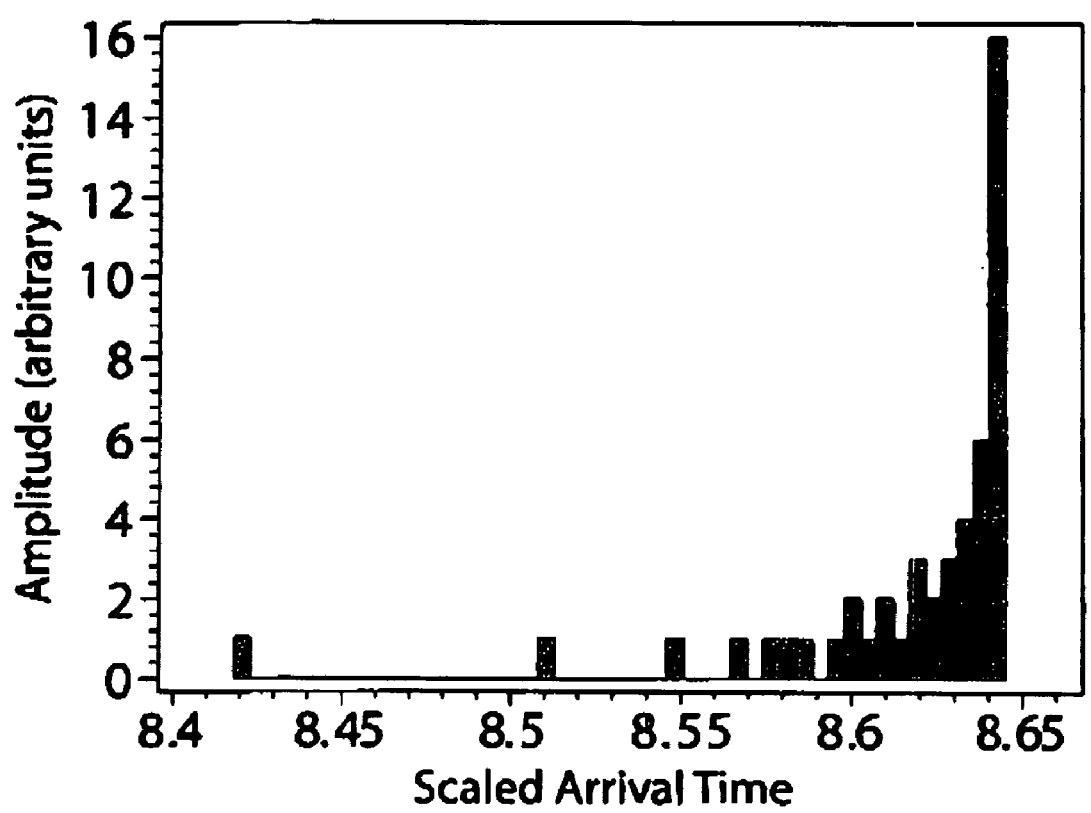

FIG. 8: Histogram of predicted arrival time (scaled by the constant $$\left(\text{scaled by the constant } \frac{L}{\mu_0 E}\right)$$

to roughly show the expected peak shape without diffusion due to the various possible locations for a single deamidation of the ssDNA-protein polymer complexes (for which $M_u$=337 and $M_c$=23 before any deamidation), investigated in reference [15]. We used $\alpha_1$=1.

FIG. 9: Structures and code names for the six different drag-tag molecules used in the experimental study. The P1-169 and P2-127 drag-tags had maleimide functionalites added to their N-termini by activation with Sulfo-SMCC, as described in Reference [24].

Figure 10:
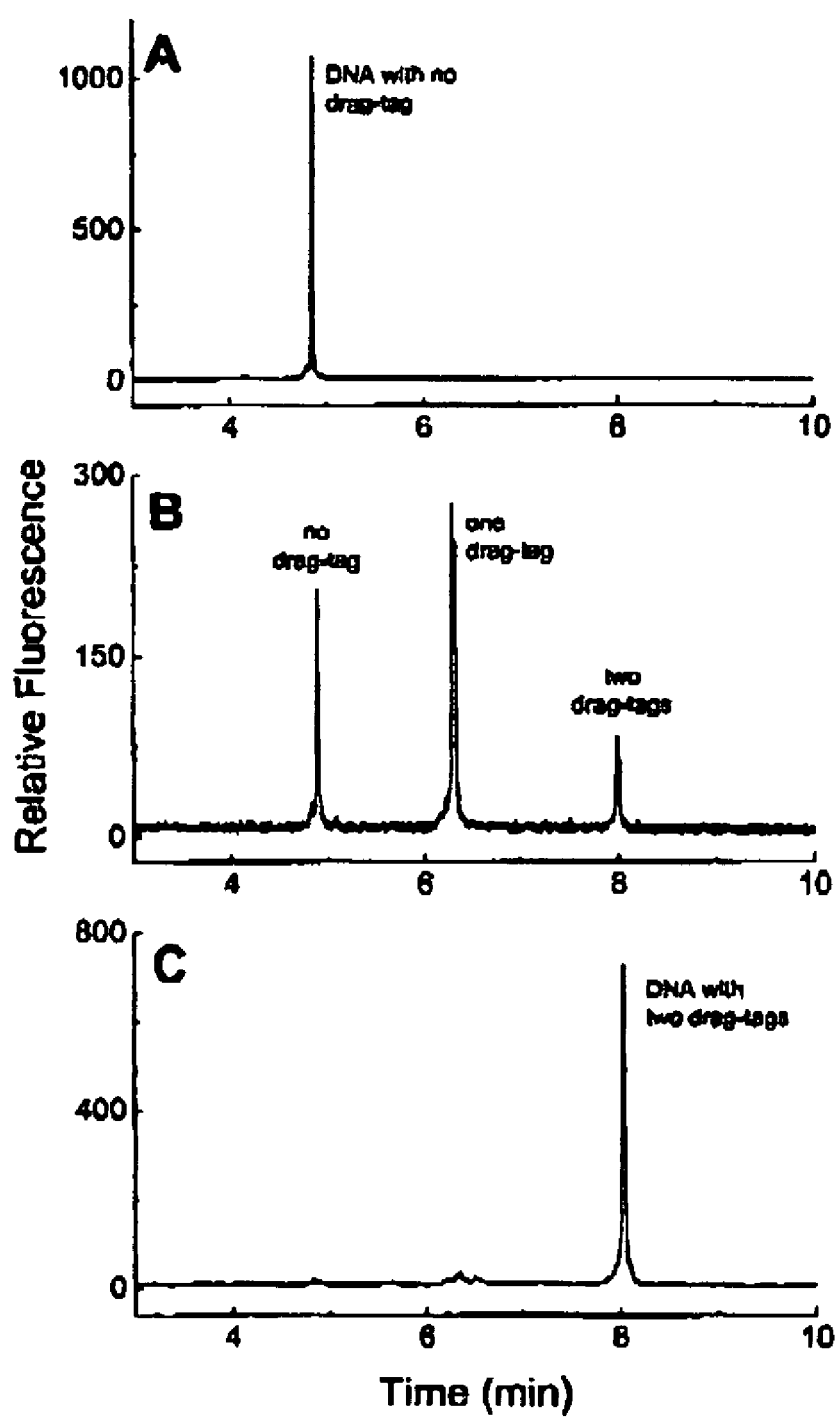

FIG. 10: T40-dithiol DNA (A) capped at both ends with excess maleimide to create unlabeled ssDNA, (B) mixed with a 15:1 molar excess of NMEG-40 drag-tag followed by excess maleimide to create a mixture of unlabeled ssDNA and ssDNA with one or two drag-tags, and (C) mixed with a 100:1 molar excess or NMEG-40 drag-tag to create doubly labeled ssDNA. Samples were analyzed on an ABI 3100 capillary array instrument in 47 cm capillaries (36 cm to detector) in 89 mM Tris, 89 mM TAPS, 2 mM EDTA buffer, pH 8.5, with 1% v/v POP-6 polymer as a dynamic coating. Samples were injected electrokinetically at 22 V/cm for 3 seconds (A) or 2 seconds (B and C), and run at a field strength of 320 V/cm, with a current of 15 µA per capillary.

Figure 11:
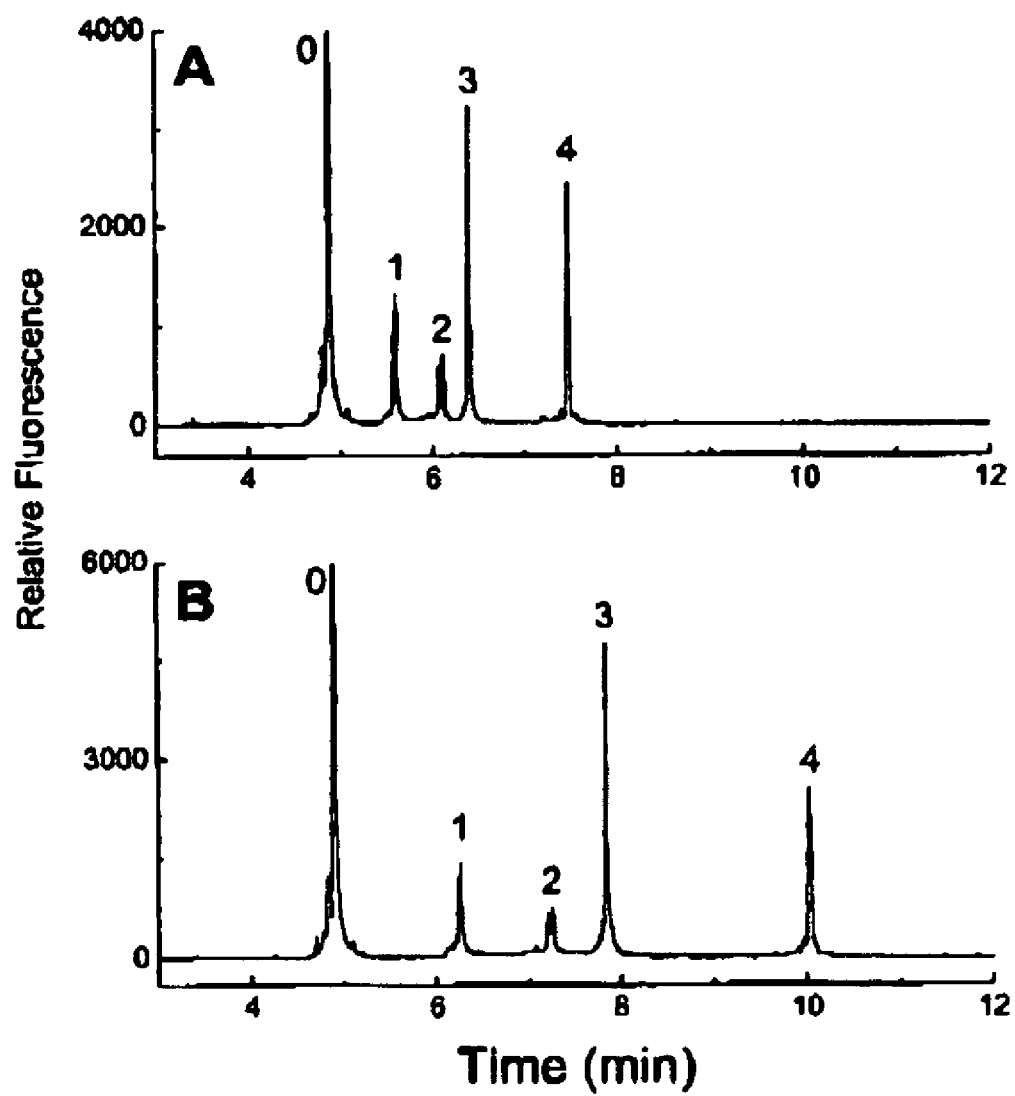

FIG. 11: Capillary Electrophoresis (CE) analysis of mixtures of 20mer and 40mer DNA with (A) NMEG-20 drag-tag, and (B) NMEG-40 drag-tag. Analysis conditions are the same as for FIG. 10, except the injection was 22 V/cm for 15 seconds. The running current was 15 µA per capillary. Peak assignments for both (A) and (B) are: 0=maleimide-capped DNA (no drag-tag); 1=40mer DNA with one drag-tag; 2=2mer DNA with one drag-tag; 3=40mer DNA with two drag-tags, 4=20mer DNA with two drag-tags.

Figure 12:
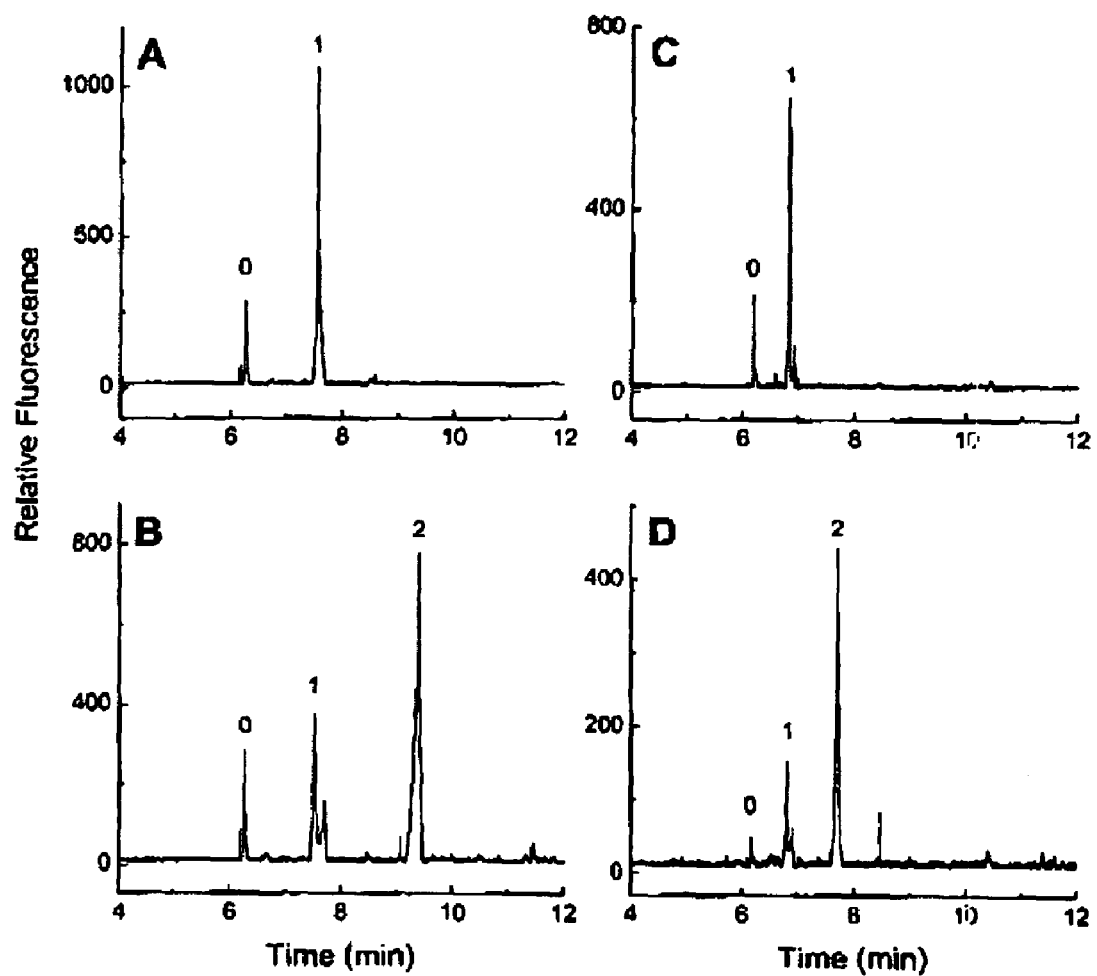

FIG. 12: Electropherograms of dsDNA conjugated to P2-127 drag-tag. (A) 100-bp PCR product with forward primer thiolated, (B) 100-bp PCR product with both primers thiolated, (C) 200-bp PCR product with forward primer thiolated, and (C) 200-bp PCR product with both primers thiolated. Analysis conditions were the same as for FIG. 10, except the run temperature was 25° C. and the injection was 1 kV for 20 seconds. Peaks labeled 0, 1, and 2 refer to DNA species with zero, one, or two drag-tags, respectively.

Figure 13:
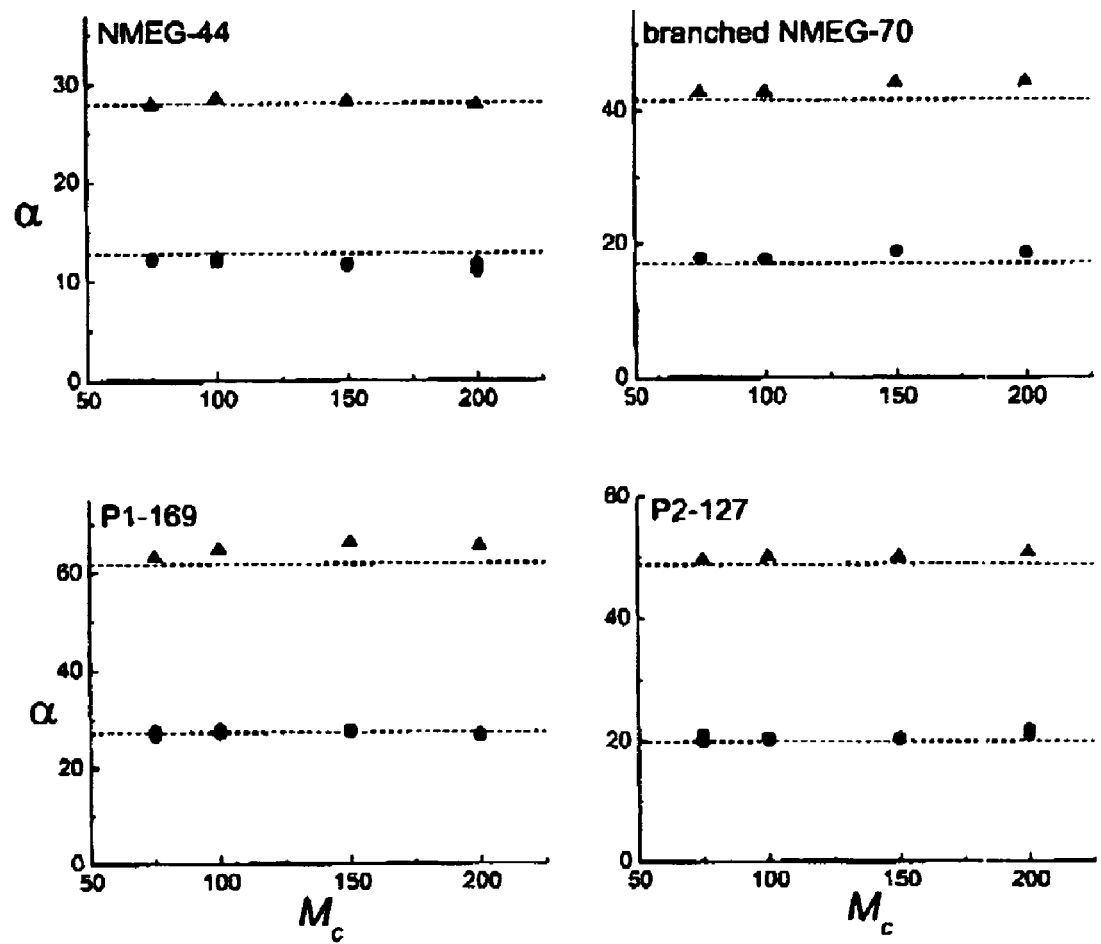

FIG. 13: Total $\alpha=\alpha_1 M_u$ values calculated for different sizes $M_C$ of dsDNA with one (●) or two (▲) drag-tags. The horizontal lines show the average α values calculated from a linear fit of $\mu_0/\mu$ vs. $1/M_C$, as given in Table 4.

Figure 14:
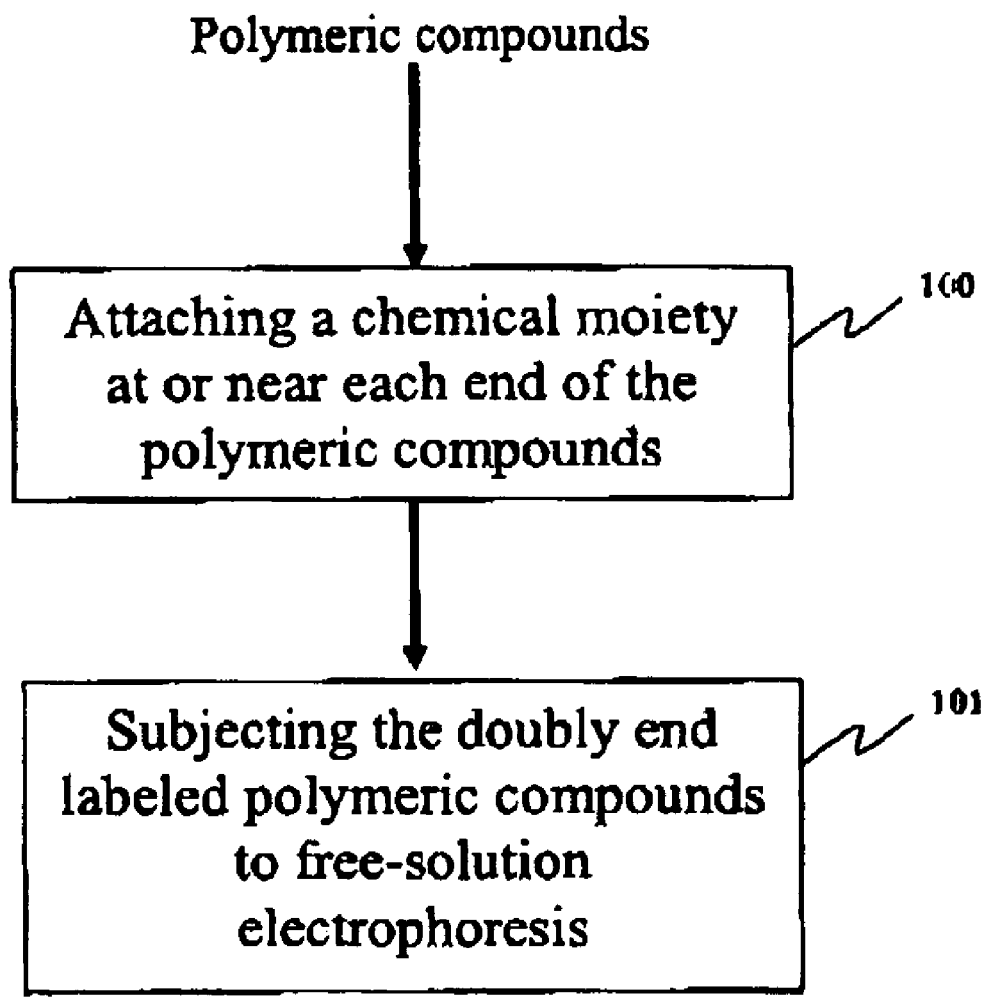

FIG. 14 provides a flow diagram of a preferred method of the invention.

FIG. 15 provides a flow diagram of a preferred method of the invention.

DEFINITIONS

'Drag'—whether used as a noun or as a verb, 'drag' refers to impedance of movement of a molecule through a viscous environment (such as an aqueous buffer), such as for example during electrophoresis, either in the presence or the absence of a sieving matrix.

ELFSE—End Labeled Free Solution Electrophoresis. The preferred conditions for ELFSE are apparent to a person of skill in the art upon reading the present disclosure, and the references cited herein 'End effect'—refers to the increased weighting monomer units located at or near the end of a polymeric molecule subjected to ELFSE. In preferred embodiments the weighting may be the numerical function $\Psi(n/N)$ given in [14] when represented, for example, by the following normalized interpolation function, shown in FIG. 1:

$$\Psi(n/N)=-0.65+0.62/(n/N)^{1/4}+0.62/(1-n/N)^{1/4}. \quad (3)$$

The inventors note that $\Psi(n/N)$ increases substantially for monomers within about the first and last ~8% of the chain (e.g., these sections would account for 24% of the total weighting of the molecule, compared to the 16% expected by the uniformly weighted average approximation). Without wishing to be bound by theory, the inventors consider this a consequence of monomers located close to the ends of the chain spending more time, on average, closer to the surface of the coil, and hence affecting the overall mobility more than the middle monomers. As a result the mobility is a weighted average of all individual monomer mobilities, where monomers in die middle have approximately the same weighting, but monomers near the end have a much greater weighting. This is the end effect which was neglected in previous ELFSE [5, 6] and FSCE [11, 13] analyses, where a uniform weighting, the dotted line in FIG. 1 was taken as an approximation (see Eq. (1)).

EOF—Electroosmotic Flow

FSCE—Free Solution Conjugate Electrophoresis

'Label' or 'tag' or 'drag-tag': refers to any chemical moiety that may be attached to or near to an end of a polymeric compound to increase the drag of the complex during free solution electrophoresis, wherein the drag is caused by hydrodynamic friction. In selected examples, the drag tag may comprise a linear or branched peptide or a polypeptoid comprising up to 300, preferably up to 200, more preferably up to 100 polymer units.

MALDI-TOF—Matrix-Assisted Laser Desorption/Ionization Time-of-Flight

'Near'—In selected embodiments of the invention end labels are described herein as being attached at or near to each end of a polymeric compound. In this context the term 'near' refers to attachment of a tag or chemical moiety to a monomeric unit in the vicinity of an end of the polymeric compound, such that the presence of the moiety or tag influences the "end effect" in accordance with the teachings of and discussions of the present application. In addition, the term "near" may vary in accordance with the context of the invention, including the size anti nature of the moiety or tag, or the length and shape of the polymeric compound. For example, in the case of a short polynucleotide comprising less than 21) bases, the to term "near" may, for example, preferably include those nucleotides within 5 nucleotides from each end of the polynucleotide; However, in the case of a longer polynucleotide comprising more than 100 bases then the term "near" may, for example, include those nucleotides within 20 nucleotides from each end of the polynucleotide.

PEG—Poly(Ethylene Glycol)

'Polymeric compound'—refers to any polymer whether of biological or synthetic origin, that is linear or branched and composed of similar if not identical types of polymer units. In preferred embodiments, the polymeric compounds are linear, and in more preferred embodiment the polymeric compounds comprise nucleotides or amino acids.

'Polypeptoid'—a linear or non-linear chain of amino-acids that comprises at least one non-natural amino acid that is not generally found in nature. Such non-natural amino acids may include, but are not limited to, D-amino acids, or synthetic L-amino acids that are not normally found in natural proteins. In preferred embodiments, polypeptoids are not generally susceptible to degradation by proteinases such as proteinase K, since they may be unable to form a protease substrate. In selected embodiments, polypeptoids may comprise exclusively non-natural amino acids. In further selected embodiments, polypeptoids may typically but not necessarily form linear or alpha-helical (rather than globular) structures. 'Preferably' and 'preferred'—make reference to aspects or embodiments of the inventions that are preferred over the broadest aspects and embodiments of the invention disclosed herein, unless otherwise stated.

DETAILED DESCRIPTION OF THE PREFERRED EMBODIMENTS

Polymeric compounds, such as polypeptides and polynucleotides, are routinely subject to modification. Chemical synthesis or enzymatic modification can enable the covalent attachment of artificial moieties to selected units of the polymeric compound. Desirable properties may be conferred by such modification, allowing the polymeric molecules to be manipulated more easily. In the case of DNA, enzymes are commercially available for modifying the 5' or 3' ends of a length of ssDNA, for example to phosphorylate or dephosphorylate the DNA. In another example, biotinylated DNA may be formed wherein the biotin moiety is located at or close to an end of the DNA, such that streptavidin may be bound to the biotin as required. Tags such as fluorescent moieties may also be attached to polynucleotides for the purposes of conducting DNA sequencing, for example using an ABI Prism™ sequencer or other equivalent sequencing apparatus that utilizes fluorimetric analysis The inventors have undertaken a thorough investigation and review of the capacity of covalently attached labels or tags to influence the frictional drag characteristics of polymeric compounds, including for example polynucleotides. Unexpectedly, the inventors have discovered that the covalent attachment of a label or tag at or near to both ends of a polynucleotide molecule can have a profound effect upon the mobility and diffusion dynamics of the molecule during free solution electrophoresis. In some way, the presence of a tag or label at each end of the molecule results in an increase in drag to a greater extent than would be expected when considering the degree of drag generated by single end modification. Through careful analysis, the inventors have delineated that this synergistic effect of double-end labeling is not an artifact or insignificant observation. Rather, it presents important opportunities for the differentiation of molecules during free solution electrophoresis. Preferably the resolution is such that single polymer units can be resolved, as would be required for example for DNA sequencing.

The methods of the invention involve End-Labeled Free-Solution Electrophoresis (ELFSE) [1,3,4,16,17]. In preferred embodiments of the invention, DNA is modified end-on with an uncharged, monodisperse, polymeric end-label or "drag-tag" to create a charged-uncharged polymer conjugate. During electrophoresis in free solution, the drag-tag imparts the bioconjugate with a fixed amount of additional hydrodynamic friction. The additional friction modifies the electrophoretic mobility of the DNA-drag-tag conjugates in a size-dependent fashion: conjugates comprising small DNA fragments migrate more slowly than conjugates with large DNA fragments, and thus a size-based separation can be accomplished in the absence of a sieving matrix.

The theoretical principles and experimental demonstrations of ELFSE have been recently reviewed [17]. In the first experimental demonstration of ELFSE, streptavidin was used to label double-stranded DNA restriction fragments that had been biotinylated at one or both ends [4]. The efficiency of this separation was limited primarily by the inherent polydispersity of the streptavidin label, as well as by interactions between the streptavidin and the capillary walls. One of the interesting results of this study, however, was that the amount of hydrodynamic drag associated with adding a streptavidin label to both ends of the DNA was observed to be more than twice the friction for adding streptavidin to one end only. Whereas a single streptavidin provided friction equivalent to an additional 23 base pairs of DNA, two streptavidins provided the friction of an additional 54 base pairs, 17% greater than would be expected from simply doubling the amount of friction from a single streptavidin. The implications of this finding were not fully appreciated at the time, and, being attributed to experimental error, this effect was not explored further.

The theoretical work of Long and co-workers [14] suggested that monomer units at or near to the ends of a polymeric compound may contribute with a greater weighting to the compound's electrophoretic mobility (when compared to other monomeric units). However, the previous practical work of the inventors, and others, has typically employed uniformly weighted averages as an approximation for the mobility of the monomer units within the test polymers. These studies neglected to take into account certain second-order effects, and in particular the so-called "end effect" discussed above. While the qualitative results for the range of data treated with the approach of Long et al. were fairly good for certain molecular sizes, the inclusion of the end effect into the theory makes significant changes for the quantitative results, and how the theory can be utilized. In particular, the inventors of the present invention demonstrate herein that the previously utilized approximation would have resulted in unrealistic molar mass profiles had it been applied to a different range of polymer sizes. Hence the end effect must be carefully accounted for when using for example FSCE for molar mass profiling of synthetic uncharged polymers. The inventors successfully apply the addition of the end effect to the theories of free solution conjugate electrophoresis and end-labeled free solution electrophoresis. More importantly, the inventors provide strong evidence that double end labeling (i.e. labeling of both ends of a polymeric compound) can give particularly desirable results in the separation of compounds by free-solution electrophoresis.

The standard theory of ELFSE has been developed through investigations into the electrophoretic mobility of polymers with non-uniform charge distributions. For the case of the migration of a DNA-drag-tag conjugate, with a charged DNA segment consisting of $M_C$ charged monomers, and an uncharged drag-tag consisting of $M_U$ uncharged monomers, the mobility $\mu$ is traditionally given by a weighted average of the electrophoretic mobilities of the charged and uncharged monomers:

$$\mu = \mu_0 \frac{M_C}{M_C + \alpha_1 M_U} \quad (2)$$

where $\mu_0$ is the mobility of the charged monomers (i.e. the free-solution mobility of DNA). (The uncharged monomers have zero electrophoretic mobility, and thus do not appear in the numerator of Equation (2)). The parameter $\alpha_1$ re-weights the number of uncharged monomers $M_U$ to reflect differences in persistence length and other hydrodynamic properties. The product $\alpha_1 M_U$, referred to as $\alpha$, describes the total friction provided by the drag-tag, in terms of the number of additional uncharged monomers of DNA that would add equivalent friction. Thus, in the experiments described previously [4], a single streptavidin drag-tag provided $\alpha=23$, i.e. an amount of friction equivalent to 23 uncharged bp of DNA, whereas two streptavidins gave $\alpha=54$. Notably, Equation (2) cannot adequately explain the more than doubling of $\alpha$ arising from using two drag-tags.

Whereas previous theory assumed that each monomer unit (after resealing the uncharged monomers by $\alpha_1$) contributes equally to the electrophoretic mobility of the composite molecule, more recent theory has taken into account end-effects originally described by Long et al. [14]. According to this theory, monomer units near either end of the polymer chain have greater influence than monomer units near the middle in determining the electrophoretic mobility of the composite molecule. This can be expressed by including a weighting factor $\Psi$ in the calculation of the mobility. For the case of ELFSE, with $M_C$ charged monomers conjugated end-on to $M_U$ uncharged monomers, and scaling $M_U$ by the factor $\alpha_1$ such that the total number of monomers is effectively $N=M_C+\alpha_1 M_U$, the weighted average mobility is expressed as:

$$\mu = \frac{1}{N} \int_0^{M_C} \mu(n) \Psi\left(\frac{n}{N}\right) dn \quad (3)$$

where the index of integration, n, represents the position of a charged monomer unit in the chain. The ratio n/N, which appears as the argument of the weighting function $\Psi$, ranges from 0 to 1, and represents the relative position of a given monomer unit in the chain. The limits of integration are written from 0 to $M_C$ (rather than 0 to N) since the uncharged monomers ($n=M_C+1$ . . . N) have zero electrophoretic mobility, and only the charged monomers contribute to the total. Making the further substitution that for charged DNA monomers, the mobility $\mu(N)=\mu_0$, and using the definition $N=M_C+\alpha_1 M_U$ the mobility of the composite molecule can be written as:

$$\mu = \frac{\mu_0}{M_C + \alpha_1 M_U} \int_0^{M_C} \Psi\left(\frac{n}{M_C + \alpha_1 M_U}\right) dn \quad (4)$$

The normalized weighting function $\Psi(n/N)$ of a Gaussian polymer chain was found by the inventors to be well-represented by the following empirical function:

$$\Psi\left(\frac{n}{N}\right) \approx -0.65 + 0.62 \left(\frac{n}{N}\right)^{-\frac{1}{4}} + 0.62 \left(1 - \frac{n}{N}\right)^{-\frac{1}{4}} \quad (5)$$

Figure 1:
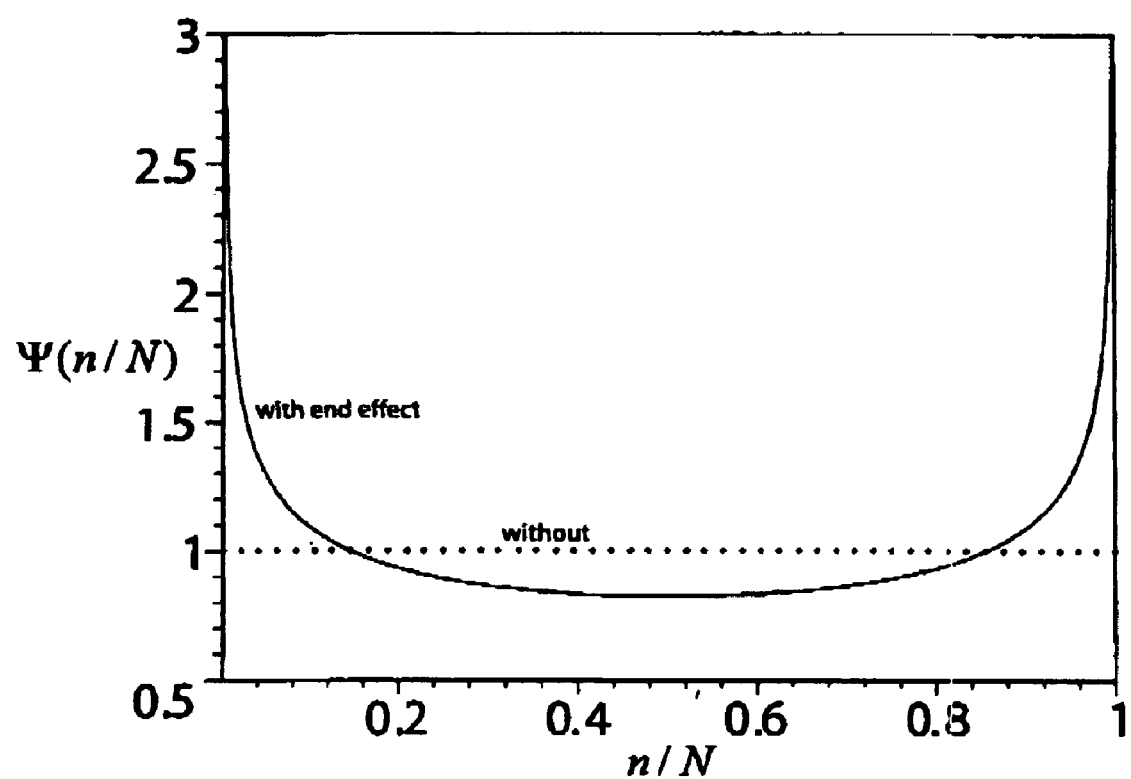
FIG. 1: End effect weighting function (Eq. (8)), an interpolating function that provides a good fit of the numerical curve presented in FIG. 2 of [14]. The dotted line is the uniform weighting approximation that was used in previous theoretical models [5, 6, 11, 13].

Equation (5) is a well-behaved, easily calculated (and easily integrated) function for $0<(n/N)<1$, and is depicted in FIG. 1 of the present application (see Examples). Using this functional form in Equation (4) allows the straightforward calculation of the electrophoretic mobility for any composite molecule consisting of a DNA chain linked end-on to an uncharged drag-tag chain, provided that the scaling factor $\alpha_1$ is known for a given set of experimental conditions.

For the slightly more complicated case of a charged DNA chain with uncharged drag-tags at both ends of the DNA chain, Equations (3) and (4) need only be modified by changing the limits of integration, and the total number of effective monomer units N. For the case of a DNA chain consisting of $M_C$ charged monomers, with identical drag-tags consisting of $M_U$ uncharged monomers at each end, the total number of effective monomers is now $N=M_C+2\alpha_1 M_U$. With this change, and inserting the appropriate limits of integration, the mobility becomes:

$$\mu = \frac{\mu_0}{M_C + 2\alpha_1 M_U} \int_{\alpha_1 M_U}^{\alpha_1 M_U + M_C} \Psi\left(\frac{n}{M_C + 2\alpha_1 M_U}\right) dn \quad (6)$$

Besides providing a more complete analysis of the electrophoretic mobility of ELFSE conjugates, and improving the quantitative analysis of previous data from the molar mass profiling of poly(ethylene glycol) [11], the theory of end-effects makes useful predictions for enhancing the performance of DNA sequencing and other separations using ELFSE. The $\Psi(n/N)$ function in Equation (5) has its maxima near the ends of the molecule, indicating that the chain ends are weighted more heavily in determining the electrophoretic mobility of the composite molecule. The heavier weighting of the chain ends implies that adding an uncharged drag-tag to each end of a DNA molecule provides more than twice the drag of using a single drag-tag of the same size at one end of the DNA molecule. This is consistent with the initial experimental observations using streptavidin as a drag-tag [4]. Moreover, since the production of very large, totally monodisperse drag-tag molecules has thus far been problematic [15, 24], the inventors demonstrate herein that the effect can be exploited to provide sufficient drag for high-efficiency separations by using two smaller (and more monodisperse) drag-tags, rather than one larger drag-tag. The present invention provides experimental confirmation of this effect using both short ssDNA oligos and larger dsDNA PCR products, with drag-tags of varying sizes at one or both ends of the DNA molecules.

In its broadest embodiment, the invention relates to the modification of any type of polymeric compound by presence of or the addition of a suitable label or tag at or near to both ends of the compound, wherein the polymeric compounds are separated by free solution electrophoresis. Any type of polymeric compound may be modified in accordance with the methods of the present invention, including non-biological and biological polymeric compounds. More preferably the compound is charged in a manner that is suitable for separation by electrophoresis. Preferably, the tags or labels are not charged such that they merely act to cause drag upon the charged polymeric compound during electrophoresis. More preferably, the polymeric compound comprises a linear series of polymer units, such as for example in DNA.

The polymeric compound is preferably a polypeptide or a polynucleotide. More preferably the polymeric compound is a polynucleotide and the method of the present invention is suitable to separate the polynucleotide from other polynucleotides of differing size. Moreover, the polynucleotide may comprise any type of nucleotide units, and therefore may encompass RNA, dsDNA, ssDNA or other polynucleotides.

In a more preferred embodiment of the invention, the polymeric compound is ssDNA, and the methods permit the separation of compounds that are identical with the exception that the compounds differ in length by a single nucleotide or a few nucleotides. In this way the methods of the present invention, at least in preferred embodiments, permit the separation and identification of the ssDNA products of DNA sequencing reactions. The size of the tag or label positioned at each end of the ssDNA molecules is (at least in part) a function of the read length of the DNA sequencing that one may want to achieve. With increasing size of labels or tags the inventors expect the methods of the present invention to be applicable for sequencing reactions wherein a read length of up to 2000 nucleotides is achieved. With other tags or labels shorter read length may also be achieved including 300, 500, or 1000 base pairs. The desired read lengths will correspond to the use to which the DNA sequencing is applied. For example, analysis such as single nucleotide polymorphism (SNP) analysis may require a read length as small as 100 nucleotides, whereas chromosome walking may require a read length as long as possible, for example up to 2000 base pairs.

Each tag or label may take any form of sufficient configuration or size to cause a sufficient degree of drag during free-solution electrophoresis. For example each label or tag may be a substantially linear, alpha-helical or globular polypeptide comprising any desired amino acid sequence. Moreover, each label or tag may comprise any readily available protein or protein fragment such as an immunoglobulin or fragment thereof, Steptavidin, or other protein generated by recombinant means. In a preferred embodiment each label or tag may be a polypeptoid comprising a linear or branched arrangement of amino acids or other similar units that do not comprise L-amino acids and corresponding peptide bonds normally found in nature. In this way the polypeptoid may exhibit a degree of resistance to degradation under experimental conditions, for example due to the presence of proteinases such as Proteinase K.

The attachment of each label or tag to the polymeric compound may occur by any suitable synthetic or enzymatic means, and may be conducted via the use of commercially available systems and kits. For example, a useful way to modify both ends of a ssDNA molecule may include the use of thiol chemistry. However, any other suitable synthetic chemistry may be used.

The invention will be further illustrated with reference to the following examples, which are in no way intended to limit the scope of the invention.

EXAMPLES

Example 1

Analysis of the Theory of Electrophoresis of Polyampholytes

As previously discussed, the electrophoretic behaviour of polymers with inhomogeneous charge distributions was previously investigated by Long and co-workers [14]. The mobility of such chains was calculated as a function of charge distribution, taking into account both hydrodynamic interactions and the elasticity of the chain. They investigated the linear regime of small electric fields where the polymer chains remain in approximately Gaussian conformation, and assumed excluded volume effects to be negligible. For uniformly charged polymers, the counter-ions effectively cancel the long range hydrodynamic interactions between monomers, such that hydrodynamic and electric forces are balanced locally, leading to the well known "free-draining" phenomenon where uniformly charged polymers migrate at the same electrophoretic velocity despite their varying lengths [7, 8]. However with non-uniformly charged polymers, it was shown that hydrodynamic interactions can play a large role. The general expression for the electrophoretic mobility of a polymer with a variable charge distribution was given as $$\mu = \int_0^N \psi(n)\mu(n)dn \quad (7)$$

where $\mu(n)$ is the mobility of the $n^{th}$ monomer, and N is the total number of monomers. The weighting function $\psi(n)$ is universal for sufficiently long polymers, i.e. it looks the same for all sizes N beyond about ten persistence lengths in that $\psi(n)=1/N\Psi(n/N)$. The inventors found that the numerical function $\Psi(n/N)$ given in [14] is represented quite well by the following normalized empirical interpolation function, shown in FIG. 1:

$$\Psi(n/N)=-0.65+0.62/(n/N)^{1/4}+0.62/(1-n/N)^{1/4}.$$

The inventors note that $\Psi(n/N)$ increases substantially for monomers within the first and last ~8% of the chain (e.g., these sections would account for 24% of the total weighting of the molecule, compared to the 16% expected by the uniformly weighted average approximation). This is a consequence of monomers located close to the ends of the chain spending more time, on average, closer to the surface of the coil, and hence affecting the overall mobility more than the middle monomers. As a result the mobility is a weighted average of all individual monomer mobilities, where monomers in the middle have approximately the same weighting, but monomers near the end have a much greater weighting. This is the end effect which was neglected in previous ELFSE [5, 6] and FSCE [11, 13] analyses, where a uniform weighting, the dotted line in FIG. 1 was taken as an approximation (see Eq. (1)). This effect may indeed be of importance when analyzing data for charged-uncharged block co-polymers, especially if one of the blocks is relatively small (e.g., less than 10% of the total polymer length) and hence has a weighting determined solely by one of the "ends" of the curve in FIG. 1.

Example 2

Analysis of the End Effect for FSCE

For the case of FSCE, where only the $M_c$ charged monomers have a non-zero mobility, one can rewrite Eq. (7) as follows:

$$\mu = \int_0^{M_c} \frac{\mu(n)}{N} \Psi\left(\frac{n}{N}\right) dn \qquad (9)$$

where the monomers are labeled starting from the charged end of the chain. The mobility of the $n^{th}$ monomer $\mu(n)$, is simply the length-independent free solution ssDNA mobility $\mu_0$, and the effective total number of monomers N is $M_c+\alpha_1 M_u$ as before in the uniformly weighted average, such that $$\mu = \mu_0 \frac{\int_0^{M_c} \Psi\left(\frac{n}{M_c+\alpha_1 M_u}\right) dn}{M_c+\alpha_1 M_u} \qquad (10)$$

Figure 2:
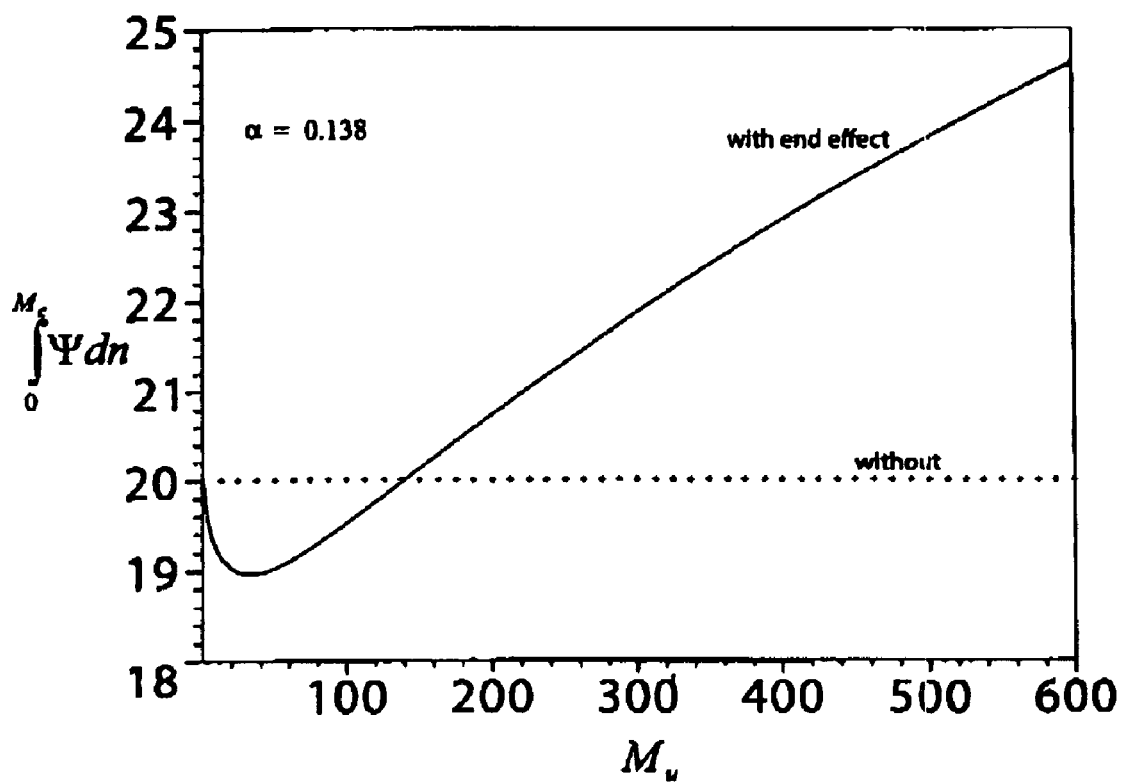
FIG. 2: Integral of end effect weighting function $\Psi$, from $n=0$ to $M_c$, for FSCE with a charged ssDNA segment of $M_c=20$ bases plotted as a function of the number $M_u$ of monomers of PEG ($\alpha_1=0.138$). Neglecting the end effect would give a constant value of 20, indicated here by the horizontal dashed line.

On comparison with Eq. (1) it is clear that taking the end effect into account involves replacing the numerator ($M_c$) with the integral of $\Psi$ over all the charged monomers (i.e. replacing the uniform weighting of $\Psi=1$ which would give $$\int_0^{M_c} \Psi \, dn = M_c,$$

with the $\Psi$ function of FIG. 1). As one can expect from the form of the $\Psi$ function, in going from a molecule that is completely charged to one that is attached to an uncharged chain, the higher relative weighting of one of the charged ends is lost and hence the end effect is manifested by an initial drop in the integral of $\Psi$ as $M_u$ increases. However as the uncharged segment grows quite large, the proportion of the conjugate molecule which is charged ($M_c/N$) decreases significantly, and the weighting for each of the charged monomer mobilities is determined solely by the remaining higher end weighting. Consequently, as the uncharged segment becomes much larger than the charged segment, the latter is given a higher weighting in the average determining the total mobility, thereby increasing the mobility over that expected by neglecting the end effect. This is indeed what is seen in FIG. 2 when the integral of $\Psi$ is plotted for the specific case studied by Vreeland et al. [11] of a 20 base ssDNA fragment ($M_c=20$) attached to various lengths of poly(ethylene glycol) (PEG), for which $\alpha_1$ was estimated to be approximately 0.138 (to be discussed later). The integral in the mobility equation initially decreases for small PEG molecules, and then increases for the larger molecules. This factor grows well beyond the value of 20 previously taken as an approximation (neglecting end effects). For the longest PEG chains examined by Vreeland et al, which have a molecular mass of about 24 kDa (corresponding to about 550 monomers), we estimate that the integral of $\Psi$ is about 24, significantly higher than the previous approximation of 20.

Figure 3:
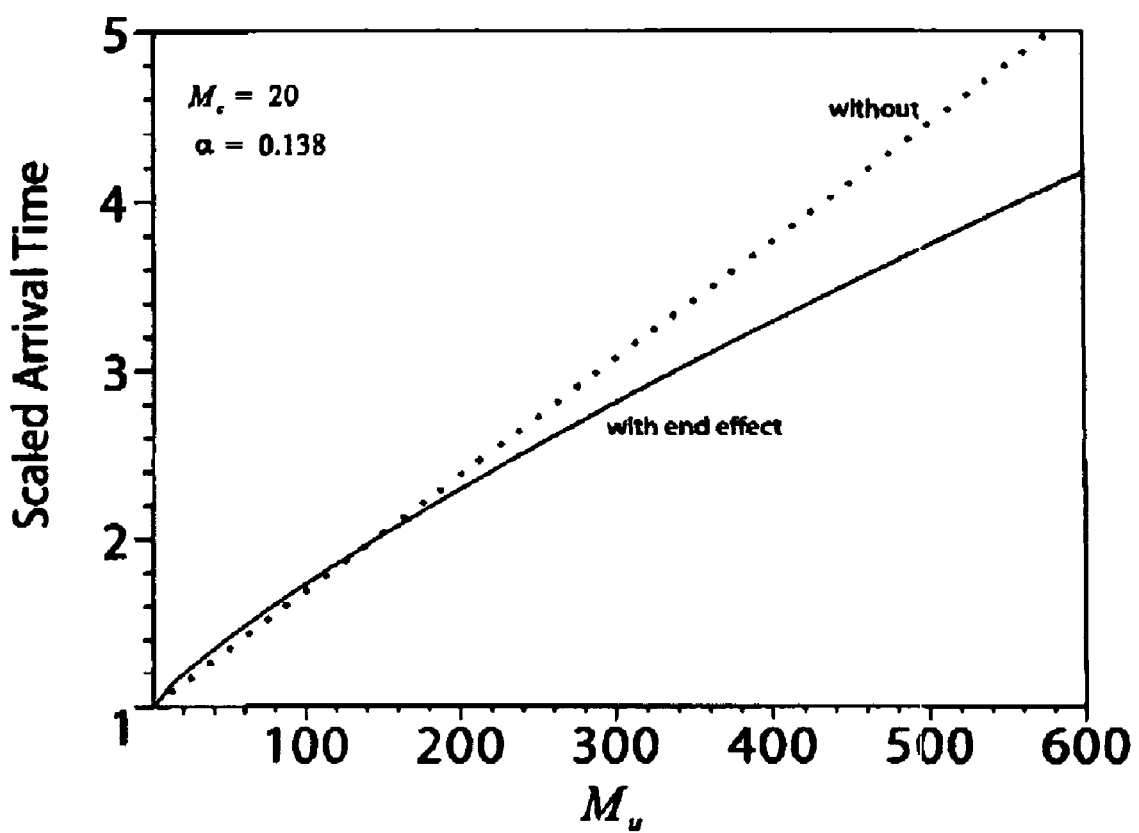
FIG. 3: Predicted arrival time at detector (scaled by the constant $$\left(\text{scaled by the constant } \frac{L}{\mu_0 E}\right)$$

The mobility of the conjugates varies not only with the weighting of the engine, but also with the total size: clearly molecules with larger uncharged segments move more slowly (this is the very means of separation). We take the mobility from Eq. (10) to find the arrival time of the molecule at the detector:

$$t = \frac{L}{\mu_0 E} \times \frac{M_c+\alpha_1 M_u}{\int_0^{M_c} \Psi\left(\frac{n}{M_c+\alpha_1 M_u}\right) dn} \qquad (11)$$

where L is the length to the detector, and E is the electric field intensity. FIG. 3 shows how the arrival time (scaled by the constant $$\frac{L}{\mu_0 E}$$

which is the elution time of naked ssDNA, i.e. for molecules with $M_u=0$) depends on the end effect. When the end effect is neglected, we see a straight line (as reported by Vreeland et al. [11] for narrow ranges of PEG molecular size). However, taking into account the end effect results in a slightly higher slope for very small PEG segments, which decreases as the size of the PEG grows, becoming significantly less than it would be were the end effect not at play. As expected, the end effect gives a higher weighting to the charged engine such that molecules (having more than 140 PEG monomers in this example) go faster than if the end effect is neglected, and increasingly so for larger conjugates where the engine weighting is pushed further to the left on FIG. 1. Unfortunately this increased speed has a negative impact on separation: for the same separation length L and field intensity E, the molecules have less time for their differences in speed to slow one relative to another. The predicted temporal peak spacing $$\left|\frac{\partial t}{\partial M_u}\right|$$

is shown in FIG. 4 for both an ssDNA engine size of $M_c=20$, and one of size of 10, which was previously predicted to be the optimal engine size [13]. Without end effects we would expect a horizontal line (one of the more interesting features of FSCE); however with end effects we see that peak spacing decreases with increasing conjugate size. For the larger molecules studied by Vreeland et al. (around 550 monomers conjugated to a 20 base DNA engine), we estimate that the end effect reduces the peak spacing to only 63% of that expected were there no end effect (see FIG. 4a). This decrease is even more pronounced for shorter charged segments; for an engine size of $M_c=10$ (FIG. 4b), the inventors predict that the peak spacing for the larger molecules would drop to a mere 54% of that previously expected. Note that even though the end effect plays a more detrimental role for the shorter engine, the overall peak spacing is still higher. As well, it should be noted that for conjugates with small uncharged segments, the end effect could be exploited as it actually leads to an important increase in separation under these conditions.

Here the inventors illustrate the manifestation of the end effect in the published FSCE experimental data [11], which previously went unnoticed. The decrease in the slope of arrival time (FIG. 3) is slow, hence over a small range of sizes the size-dependence of the arrival time could easily appear to be linear; this was indeed what Vreeland et al. reported [11]. The measured arrival times were linear for both PEG molecular size ranges, the smaller sizes ranging from approximately 4.5 kDa through 7 kDa (corresponding to about $M_u=100$ through 160 PEG monomers) and the larger ranging from about 20 kDa through 24 kDa (about $M_u=450$ through 550 PEG monomers). As previously mentioned, the approach taken for the data analysis was to neglect the end effect by assuming the $\Psi$ weighting function to be uniform (see Eq. (1)). Hence by neglecting the $\Psi$ dependence on $\alpha_1 M_u$, this term could be isolated from the mobility expression, $$\alpha_1 M_u = M_c \left[\frac{\mu_0}{\mu} - 1\right]$$

and plotted as a function of peak number (which varies linearly with the number of PEG monomers $M_u$ since FSCE yields single monomer resolution). The slope of this plot, which is basically a scaled arrival time, was then simply taken to be $\alpha_1$. This value was then used to calculate the molar masses of both samples since it should not depend on the length of the polymers, rather just their individual monomer lengths and flexibilities. As we can see from FIG. 3, while the slopes of the arrival times with and without the end effect taken into account diverge for larger PEG sizes, they are fairly similar for $M_u \approx 100$-160 monomers. Hence the approximation used to determine $\alpha_1$ from the data by neglecting the end effect may be reasonable for these small sizes; however one would expect it to be poor for the larger sizes for which the end effect has a more critical impact. Fortunately, when the approximation of neglecting the end effect was used [11], $\alpha_1=0.138$ was in fact determined using only the small sizes range ($M_u \approx 100$-160 monomers) and then this value was used to calculate the molar mass profiles for all sizes. As a result of this somewhat lucky choice for the size range to determine $\alpha_1$, very good agreement with MALDI-TOF analyses of molar masses was achieved; for example, FSCE gave a (number) average molar mass of $M_n=5735$ g/mol, while MALDI-TOF, the industry standard, gave $M_n=5728$ g/mol for the small sizes range [11]. In fact, for all PEG sizes conjugated to an engine of 20 bases, FSCE molar masses agreed with MALDI-TOF results to within a 3.2% difference, supporting the use of the $\alpha_1$ value of 0.138 determined from the small sizes. If however one had used the FSCE data for the larger PEG sizes ($M_u \approx 450$-550 monomers) to determine $\alpha_1$ under the approximation of neglected end effects, good results would not have been achieved. FIG. 3 suggests that the slope of the arrival time for these larger sizes is significantly less than expected by neglecting the end effect. Hence the $\alpha_1$ value obtained by this approximation, i.e. from the scaled arrival time slope, would be expected to be less than that of the small sizes. Using the approximation of neglected end effect to determine $\alpha_1$ from the larger sizes would have lead to erroneous molar mass calculations from FSCE data, i.e. $M_u=9652$ g/mol instead of $M_n=5728$ g/mol from MALDI-TOF, for the small sizes range. This means a 69% difference, compared to the mere 0.12% difference from using the $\alpha_1$ value determined from the smaller PEG sizes for which the end effect plays a lesser role. Clearly the end effect has a critical impact on the electrophoretic behaviour of charged-uncharged polymer complexes and must be taken into account to ensure accurate determinations of molar mass from FSCE analysis.

In the preceding development the inventors chose to use $\alpha_1=0.138$ due to the good agreement achieved between FSCE and MALDI-TOF results; however we could also determine a value for both $\alpha_1$ and $M_u$ simultaneously by solving the equation for arrival time (Eq. (11)) and its derivative with respect to $M_u$. By this approach we take the end effect into account and use only the arrival time of the conjugates at the detector and the derivative of this time with respect to peak number. (Note that the peak number varies linearly with PEG size $M_u$, as mentioned previously.) This system of two equations and two unknowns was solved numerically to yield values of $\alpha_1=0.168$ and $M_u=111$ monomers for the middle peak of the small PEG sizes (5 kDa nominal average molar mass). The results for the midpoint of the larger PEG sizes (20 kDa nominal average molar mass) were also fairly reasonable at $\alpha_1=0.129$ and $M_u=560$ monomers. The $\alpha_1$ values determined by this technique have a percent difference of 23% (as opposed to 69% using the previous approach). One possible reason for the remaining discrepancy is that experimental conditions may have changed either between runs with the shorter and larger PEGs or even during a single run. The larger PEGs take about 3 times longer to elute and hence it is possible that the electric current may drop and/or the temperature may change slightly during the course of the experiment, for example. A change in temperature would change the value of $\alpha_1$ directly since this value depends on the flexibility of the polymers, which in turn depend on temperature. If there were a drop in current between the time when the mobility of the unconjugated engine $\mu_0$, is measured and when the mobility of the conjugates $\mu$, are measured then these two values would not correspond to the same conditions as expected by Eq. (10). While the end effect is clearly manifested in the FSCE data, there is still some discrepancy between prediction and that which is observed experimentally; this may be due to changes in experimental conditions such as those mentioned above, or to second order effects not yet taken into account which will be discussed later.

Example 3

Analysis of the End Effect for ELFSE

With ELFSE, variable engine (ssDNA) lengths $M_c$ are conjugated to uncharged molecules of a set size $M_u$. In previous experimental work [5, 6, 1], the uncharged drag molecule was streptavidin, which was estimated (by neglecting the end effect) to have an effective number of monomers $\alpha_1 M_u = 36$ under the specific experimental conditions. Through conjugation with the uniform drag molecules, the various lengths of ssDNA, up to about 110 bases, were successfully sequenced in free solution [1]. Since ELFSE is used for sequencing of DNA, an exact value for alpha is not as crucial for data analysis, i.e. one need only be concerned with the sequence of arrival times, which is not changed by the end effect. However, to fully understand ELFSE data, and to make predictions for optimal sequencing conditions, the role that the end effect plays should be addressed.

The arrival time at the detector for ELFSE is given by Eq. (11), as with FSCE; here however the engine size $M_c$ is no longer constant, rather it is the uncharged segment that remains fixed. As the engine grows relative to the drag molecule, the region of the $\Psi$ curve determining its weighting expands beyond the "end" weighting to encompass more of the lower weighting of the "middle" (see FIG. 1). In FIG. 5 it can be seen that the end effect speeds up smaller molecules, while it slows down larger molecules. Again we are mostly concerned with the resolution, which depends in part on peak spacing. The end effect is expected to decrease peak spacing for the range of data previously investigated (below 110 bases); however it should start to increase peak spacing at about 115 monomers. This crossover from a negative impact on peak spacing to a positive one is shown by the ratio of predicted peak spacing with the end effect taken into account to that without; see FIG. 6. For 110 bases, there is a slight decrease in peak spacing expected due to end effects, which will quickly be replaced toy a positive effect for larger sizes. Hence this examination of the end effect bodes well for ELFSE as this technique matures, i.e. by increasing separating capacity for larger molecules over what could be expected based on data for shorter molecules, where end effects had a more pronounced negative effect.

One of the goals of current ELFSE work is to increase the size of the uncharged segment of the conjugate so as to increase the frictional drag it induces and extend the read-length, i.e. the number of bases which can be sequenced. Unfortunately for a larger "drag" molecule of 100 (rather than 36) effective monomers, the end effect would be expected to decrease peak spacing up until about 320 monomers, i.e. a crossover from a negative to positive effect at about 320 instead of 115 monomers. However, despite the farther reaching negative impact of the end effect, the greater friction of a larger drag molecule would nevertheless result in better separation. The predicted ratio of peak spacing for the hypothetical drag molecule of 100 effective monomers to that of 36 effective monomers is shown in the inset of FIG. 7. The peak spacing is significantly higher for the larger label, at least two times higher throughout the range of DNA sizes shown.

In any event, the inventors reasonably expect that the methods of the present invention may be applied to DNA sequencing reactions such that a read length of at least 500, preferably 1000, preferably 2000 nucleotides may be achieved. In this way, the methods of the invention may be applied to a wide range of applications where DNA sequencing is required, whether a short or longer read length is preferred.

Example 4

Labelling Both Ends of ssDNA for ELFSE

Another means of increasing the resolution of ELFSE would be to label both ends of the ssDNA chain with the drag molecule. This would thus give each conjugate two drag molecules, thus increasing the total friction; however in contrast to simply doubling the size of a single drag molecule, the key feature of this configuration is that the drag molecules would be given the highest weighting, that of both ends, leaving the charged section only the lower "Middle" weighting of the $\Psi$ function. Hence by placing the uncharged sections, with their null mobility, at each end, the resulting frictional drag of the conjugate is optimized; adding one label to each end of the ssDNA chain has more impact than doubling the size of a single end label. FIG. 7 shows the expected peak spacing improvement when both ends are labeled with the drag molecule of 36 effective monomers rather than just one. Clearly, having two drag molecules instead of one does not simply double the effective friction coefficient of the uncharged sections as would be expected were there no end effect, rather it increases it by a factor greater than two due to the end effect. One important finding is that, unlike the situation with only one end label, the end effect increases peak spacing for all sizes when both ends are labeled (see the inset of FIG. 6). For smaller ssDNA chains, having both ends labeled with a drag molecule of 36 effective monomers results in better peak spacing than having a single drag molecule of 100 effective monomers, whereas for larger chains, beyond 308 bases, the inverse is true (compare FIG. 7 with its inset). Since it may be difficult to find a larger drag molecule which is suitable (i.e. it would have to be water soluble and amenable to uniform conjugation to ssDNA), it may be preferable to attach two of the smaller labels as a means of improving ELFSE separation; this is one of the main findings of this work. Previously, Heller et al. [4] labeled double stranded DNA with a streptavidin molecule on one end as well as both ends. By neglecting the end effect, Heller et al. interpreted their experimental results by calculating a value of $\alpha$ for these conjugates to be 23 for a single drag molecule, but 54, rather than 46. for two drag molecules. Heller et al. provide little or no discussion of this result, and presumably attribute these experimental observations to an artifact or standard errors. While these results were misunderstood at the time, a detailed theoretical re-analysis of the data of Heller et al. by the inventors of the present invention, indicates that the end effect did in fact play a significant role in determining the overall mobility of the conjugates; labeling both ends more than doubled the effective friction coefficient, a result that could not be explained until now.

Example 5

Discussion of Examples 1-4

It is important to note that the end effect theory of Long and co-workers [14] is for random Gaussian coils. The end effect arises due to the effective "shielding" of monomers located inside the coil (on average) which leaves the ends (located closer to the outside of the coil on average) to interact more with the surrounding fluid, and thereby to have a greater effect on the overall mobility. Hence one must be careful in applying the results presented herein to very short molecules whose conformation may not yield this end effect. Also, for very large molecules, there is an excluded volume effect that is not accounted for by the random Gaussian coil approximation, which could change the predictions somewhat for these larger molecules.

There is also a small effect due to the hydrodynamic interactions between adjacent monomers on the chain which was not taken into account in previous theories. Although long-range hydrodynamic interactions are screened by the counter-ions, there is some coupling on a local scale between adjacent monomers [14]. As a result, uncharged monomers neighbouring charged monomers are pulled along by the hydrodynamic flow created by the electrophoretic pull on the charged monomers. This effect is highly localized and drops off exponentially with distance, however it gives an effective non-zero mobility to nearby uncharged monomers. This highly localized effect also means that the end monomers of a charged section have a slightly lesser effective mobility than those in the middle of the charged section since they do not have the additional mobility due, to the hydrodynamic flow created by the electrophoretic movement of the nearby charged monomers on both sides. Hence for the mobility in FSCE and ELFSE, the more highly weighted monomers, the ones at the end, have a slightly lesser effective mobility, while the first few uncharged monomers near the joint with the charged chain section have a slight, non-zero mobility. Hence this local hydrodynamic effect could play a role in determining the overall mobility of conjugates; for example, it could decrease the end effect slightly by decreasing the mobility of the more heavily weighted monomers, those charged monomers at the end of the molecule. However this would be in an absolute fashion in that it would not depend on the relative sizes of the different components of the molecule, unlike the end effect. For ssDNA under the conditions of ELFSE and FSCE however, the extra mobility given to the uncharged segment neighboring the ssDNA monomers, and that taken away from the first few ssDNA monomers on each end of the ssDNA segment, are expected to be negligible. However, for more flexible molecules this local hydrodynamic coupling extends over more monomers and hence this effect could be important and in preferred embodiments may be taken into consideration for the mobility of such conjugate molecules.

The inventors' re-analysis of the FSCE results, in light of the end effect predicted by Long and co-workers [14] has shown that this effect is indeed significant; it is readily visible in the data and must be taken into account when calculating the molecular mass. As the size of the uncharged polymers increases, the relative size of the engine decreases so that it receives a much greater weighting in the average determining the overall mobility. As a result, for larger molecules the predicted mobility is greater than would be expected were there no end effect. There is a corresponding decrease in peak spacing, originally assumed to be constant [11, 13], which must be taken into account when analyzing the data, especially when the peak spacing is used to determine the $\alpha_1$ value (if the uncharged polymer. In previous work [11, 13] the inventors were fortunate to use the peak spacing for the smaller PEG molecules to determine the value of $\alpha_1$ that was then used to determine the molecular masses, because the end effect had less of an impact for the smaller sizes, such that the approximation of negligible end effects was acceptable. The value of $\alpha_1$ used in the determination of the molecular masses from FSCE data is crucial and unfortunately can not be obtained as simply as previously thought. It can be calculated from the persistence lengths and monomer sizes of the two sections of the conjugate [13], although one would need to be careful to take the experimental conditions (temperature and ionic strength) into account. Another means of determining the $\alpha_1$ value would be to compare the FSCE results to MALDI-TOF results for the same polymer and find the $\alpha_1$ value that allows for agreement between the two molecular mass estimates (similar to the approach taken in this paper for assessing the accuracy of the value for $\alpha_1$). This value need only be determined once for each conjugate type and then FSCE calculations can be made independently. In addition, the simultaneous solution of the equations for the arrival time and the derivative of the arrival time provides another means of estimating $\alpha_1$. For this technique to yield accurate results, a very precise measurement must be made of the length-independent free solution ssDNA mobility $\mu_0$, as the results obtained depend quite sensitively on it. It may be best to inject unconjugated ssDNA molecules periodically throughout the migration time of the conjugates so as to monitor any changes in this value due to changes in experimental conditions during the experiment.

Although the end effect explains the decrease in peak spacing observed in FSCE data, it does not appear to completely account for the decrease. This effect is predicted (based on an $\alpha_1$ value of 0.138) to decrease the peak spacing of the larger PEG sizes (about 500 monomers) to 77% of that of the smaller PEG sizes (about 130 monomers), whereas the data shows a greater decrease: the peak spacing of the larger PEG sizes is only 59% of that for the smaller PEG sizes. This discrepancy may be due to excluded volume effects for the larger PEG sizes which were neglected by Long and co-workers when they determined the function governing the end effect [14]. Also any variation in temperature or electric current during or between experiments would change the mobility, and the former would also lead to a change in persistence length, thereby changing the $\neq_1$ value itself. A very clear demonstration of the decrease in peak spacing for larger molecules is provided by Bullock [18], where PEG with two end labels were electrophoresed in free solution. The end labeling was achieved by reacting the terminal hydroxyl groups of PEG with phthalic anhydride, thereby tagging a phthalate ester onto each end. The separation was performed under conditions of electroosmotic flow (EOF), such that there was a strong electric field driven counter-flow that caused the molecules to migrate backwards in the electric field such that the slowest became the fastest and vice versa. The change in peak spacing with molecule size is readily visible in the electropherogram, FIG. 11 in [15]; the larger PEG molecules (about 70 monomers) have a peak spacing that is less than one fifth of that of the smaller PEG molecules (about 20 monomers). Not only does this show a very clear, single data set expression of decreased peak spacing for larger conjugates, but it also confirms that the decrease in peak spacing is not due to a systematic change in experimental conditions during electrophoresis causing a decrease in peak spacing because here the EOF makes it such that the larger molecules elute first.

The end effect is also very important for ELFSE since it can greatly increase, or reduce peak spacing depending on the conditions of the experiment. Once the desired sequencing length is chosen, the end effect can be taken into account in order to determine the necessary label configuration. The end effect is predicted to increase peak spacing for molecules just beyond the range of current experimental data [1], and hence affects predictions of optimal performance.

Having a precise value for $\alpha_1$ is not as much of an issue as it is for FSCE because with ELFSE the ssDNA is being sequenced and hence the length is known. This value may be important however for system optimization and other theoretical analyses; for example the inventors have found that attaching the small label (of effective size 36) that has been used experimentally thus far, to both ends of the ssDNA would result in better peak spacing than could be achieved through one single larger label (of effective size 100), under certain conditions. This remarkable result could not have been expected without taking the end effect into account.

The end effect not only has a critical impact on the electrophoretic behaviour of charged-uncharged polymer complexes, but it also affects polymers with variable charge distributions. Due to the end effect, a polymer having more of its charges located near the end(s) would have a higher electrophoretic mobility than if its charges were located at the middle of the chain. Recently a technique similar to FSCE was used to study glutamine deamidation in a long polypeptide [16]. The extent to which glutamine deamidation occurs varies with the extent of exposure to cyanogen bromide cleavage reaction mixture. In order to assess the degree of deamidation, a uniform DNA engine was conjugated to the protein polymer for electrophoresis. The latter however, was also of a set length, but it had a varying charge distribution due to the negative charge of the deamidated glutamic acid residue(s). In this study there were 48 potential sites for deamidation spaced evenly throughout the protein polymer and it was assumed that deamidation occurred randomly over these sites. The electrophoretic separation revealed varying electrophoretic mobilities even though the complexes were all of the same length, because of the varying extents of deamidation: the greater the extent of deamidation, the greater the charge and hence the higher the mobility. However, for each degree of deamidation the end effect would also result in a spread in mobilities based on the location of the deamidation site along the chain. Even for a single negative charge resulting from a single deamidation, the 48 possible locations for the charge, some near the end, others near the middle of the conjugate, would allow for a spread in mobilities. This spread is due to a constant velocity difference between the molecules with different deamidation locations, and hence the peaks would be expected to broaden linearly with time even in the absence of diffusion. The peak shape for a single deamidation is roughly predicted to be that presented in FIG. 8. This rough peak shape was obtained by approximating $\alpha_1=1$, and taking the mobility of a deamidated glutamic acid residue to be about that of single-stranded DNA. Each location for the negative charge due to deamidation is expected to have equal probability. To obtain the expected peak shape we used a histogram that would collect the number of conjugates arriving at the detector within a set amount of time. Clearly there are some conjugates that have a much higher mobility (and hence shorter arrival time); these faster molecules have their deamidation induced negative charge located near the end of the chain and hence the end effect gives it a greater weighting in the mobility. These faster molecules may even be lost in the peak corresponding to the next level of deamidation. This may explain some of the peak shapes observed in [16]. Hence the end effect may also be of interest in analyzing electropherograms of uniform length molecules with varying charge distributions.

Example 6

Chemicals and Drag-Tag Molecules

In the subsequent examples, the following chemicals and drag-tag molecules were utilized:

Tris(2-carboxyethylphosphine) (TCEP) and maleimide were purchased from Acros Organics (Morris Plains, N.J., USA). Sulfosuccinimidyl 4-N-maleimidomethyl cyclohexane-1-carboxylate (Sulfo-SMCC) was purchased from Pierce (Rockford, Ill., USA). Buffer salts Tris (free base), N-tris[hydroxymethyl]methyl-3-aminopropanesulfonic acid (TAPS), and EDTA were purchased from Amresco (Solon, Ohio, USA). POP-6 polymer solution was purchased from Applied Biosystems (Foster City, Calif., USA). All water was purified using an E-Pure system from Barnstead (Boston, Mass., USA) to a minimum resistivity of 17.8 MΩ-cm.

Six different drag-tag molecules were used in the subsequent examples. Three were linear N-methoxyethylglycine (NMEG) oligomers of length 20, 40, or 44 monomers, produced by a solid-phase submonomer synthetic protocol [19], capped with an N-terminal maleimide, and purified to monodispersity by RP-HPLC as described previously [12, 20, 21]. Another drag-tag used was a monodisperse branched molecule consisting of a 30mer poly(NMEG) backbone with five octamer oligo (NMEG) branches, also described previously [22]. The final two drag-tags were repetitive protein polymers of length 127 and 169 amino acids, produced using the controlled cloning technique [23], and activated at the N-termini using the heterobifunctional crosslinker Sulfo-SMCC by reacting the protein polymers with a 10-fold molar excess of Sulfo-SMCC for one hour at room temperature and pH 7.2, and then removing excess crosslinker by gel filtration as described previously as described previously [24, 15]. The structures and short names of the drag-tags are shown in FIG. 9. The NMEG-20 and NMEG-40 drag-tags were used for the studies of ssDNA, whereas the larger tags were used for the studies of dsDNA. All of the drag-tags used are hydrophilic, water-soluble molecules. Following the maleimide activation of the N-termini, the NMEG drag-tags are charge-neutral, whereas the P1-169 has a net charge of −1 (from deprotonation of the C-terminus), and the P2-127 (with two cationic arginine residues) has a net charge of +1.

Example 7

Production of ssDNA Conjugates

Two poly(dT) oligonucleotides of length 20 and 40 bases were purchased from Integrated DNA Technologies (Coralville, Iowa, USA). The oligos were modified at the 5' end with a thiol linker that has a 6-carbon spacer, and at the 3' end with a thiol linker having a 3-carbon spacer. The oligos were also modified internally with a fluorescein-dT base near the middle of the chain. These dithiolated, fluorescently labeled oligos (referred to as T20-dithiol and T40-dithiol) are shown schematically in Table 1.

TABLE 1

Oligonucleotides used for producing ssDNA conjugates with drag-tags at one or both ends.
$X_1$ = 5'-thiol linker with 6-carbon spacer,
$X_2$ = internal fluorescein-dT base, $X_3$ = 3'-thiol linker with 3-carbon spacer.

| Oligonucleotide | Sequence |
|---|---|
| T20-dithiol | $X_1$ TTTTTTTTTX$_2$ TTTTTTTTTT X$_3$ |
| T40-dithiol | $X_1$ TTTTTTTTTT TTTTTTTTTX$_2$ TTTTTTTTTT TTTTTTTTTT X$_3$ |

The thiol linkers on the DNA oligos were reduced using TCEP. To accomplish this reduction, 400 pmol of the dithiolated ssDNA (either T20-dithiol or T40-dithiol) was mixed with a 40:1 molar excess of TCEP, in a total volume of 10 µL of sodium phosphate buffer (100 mM, pH 7.2). This mixture was incubated at 40° C. for 2 hours. The reduced DNA was then split into aliquots of 10 pmol each prior to the addition of the drag-tag. To one aliquot, a large excess of maleimide (5 nmol) was added, capping the reduced thiols, and creating ssDNA molecules with no drag-tag (except the maleimide). To another aliquot, a large excess of drag-tag (1 nmol of either NMEG-20 or NMEG-40) was added, such that the majority of ssDNA molecules would have polymeric drag-tags at both ends. The other aliquots were treated with different amounts of drag-tag, from 50-200 pmol, with the intent of creating mixtures containing appreciable amounts of DNA with zero, one, or two drag-tags. After reacting for approximately 90 minutes, an excess of maleimide (5 nmol) was added to these reactions to cap any remaining free thiols. The reactions were incubated in the dark at room temperature for at least four hours prior to CE analysis.

Example 8

Production of dsDNA Conjugates

Oligonucleotides used as PCR primers were purchased from Integrated DNA Technologies, and are shown schematically in Table 2.

TABLE 2

Oligonucleotides used as PCR primers for producing dsDNA conjugates with drag-tags at one or both ends. $X_1$ = 5'-thiol linker with 6-carbon spacer, $X_2$ = internal fluorescein-dT base.

| Oligonucleotide | Sequeuce |
|---|---|
| M13-Forward | $X_1$ CC$X_2$TTTAGGG TTTTCCCAGT CACGACGTTG |
| 75-Reverse | GAGTCGACCT GCAGGCATGC |
| 75-Reverse-T | $X_1$ GAGTCGACCT GCAGGCATGC |
| 100-Reverse | GAGCTCGGTA CCCGGGGATC |
| 100-Reverse-T | $X_1$ GAGCTCGGTA CCCGGGGATC |
| 150-Reverse | GCGGATAACA ATTTCACACA |
| 150-Reverse-T | $X_1$ GCGGATAACA ATTTCACACA |
| 200-Reverse | CCAGGCTTTA CACTTTATGC |
| 200-Reverse-T | $X_1$ CCAGGCTTTA CACTTTATGC |

The oligonucleotides consist of an M13 forward primer with a 5'-thiol linker and an internal fluorescein-dT base, and a set of M13 reverse primers, with or without 5'-thiol linkers, designed to produce dsDNA products of 75, 100, 150, or 200 bp in size when used in a PCR reaction with the forward M13 primer.

PCR reactions were performed using Pfu Turbo polymerase (Stratagene, La Jolla, Calif., USA). Eight reactions were carried out with 20 pmol of the fluorescently labeled, thiolated M13 forward primer, and 20 pmol of each of the M13 reverse primers shown in Table 2, in a total volume of 20 µL. M13 control DNA from a sequencing kit (0.2 µL) (Amersham Biosciences, Piscataway, N.J., USA) was used as a template. The M13 template was PCR-amplified with 32 cycles of denaturation at 94° C. for 30 seconds, followed by annealing at 54° C. for 30 seconds and extension at 72° C. for 60 seconds. Products were analyzed by 2.5% agarose gel electrophoresis to confirm the sizes of the dsDNA amplicons, and the products were stored at −20° C. until subsequent use.

Thiolated PCR products were reduced using a large excess of TCEP. To do this, 7 µL of PCR product was mixed with 0.7 µL of 1M TCEP (in 1M Tris buffer), plus an additional 0.35 µL of 1M Tris, resulting in a solution of pH ~5. This mixture was incubated for 2-2.5 hours at 40° C. Excess TCEP as well as PCR reaction components were removed using QIAquick PCR purification spin columns (QIAgen, Valencia, Calif., USA) according to the manufacturer's instructions, with elution of the purified DNA in 30 µL of 100 mM sodium phosphate buffer, pH 7.2.

The purified PCR products (with one or two reduced thiols, depending on the reverse primers used) were split into multiple aliquots, and treated with one of four maleimide-activated drag-tags: NMEG 44 branched NMEG-70, P1-169, or P2-127. The amounts of drag-tag were sufficient in most cases to produce significant quantities of DNA with one or two drag-tags. Additional aliquots were treated with excess maleimide, to simply cap the reduced thiols and prevent further reaction or dimerization.

Example 9

CE Analysis of Conjugates

Free-solution CE analysis was performed using an Applied Biosystems Prism 3100 Genetic Analyzer (Applied Biosystems, Foster City, Calif., USA), using an array of 16 fired silica capillaries with inner diameter of 50 µm, and a total length of 47 cm (36 cm to the detector). The running buffer was 89 mM Tris, 89 mM TAPS, 2 mM EDTA, pH 8.5, and 1% v/v POP-6 polymer solution to act as a wall-coating agent, with the adsorbed poly(dimethylacrylamide) effectively suppressing the electroosmotic flow [25]. (The resulting polymer concentration is very low, and does not lead to any size-based sieving of the DNA.) samples were diluted in water prior to analysis, to provide signals of appropriate strength for the fluorescence detector. The ssDNA samples were analyzed at 55° C., whereas dsDNA samples were analyzed at 25° C. to prevent denaturation. Samples were introduced into the capillaries by electrokinetic injection at 1 kV (22 V/cm) for 2-20 seconds. Separations were carried out at 15 kV (320 V/cm). The fluorescein label of the DNA was detected in the "G" channel of ABI Dye Set E5, with $\lambda_{max} \approx 530$ nm.

Example 10

Analysis of ssDNA Conjugates

The experimental protocol in which ssDNA was mixed with different amounts of maleimide-activated drag-tag allowed the successful production of species with zero, one, or two drag-tags, which were easily separated and identified by free-solution CE analysis. This is illustrated in FIG. 10 for the case of the T40-dithiol DNA with NMEG-40 drag-tags. As seen in FIG. 10A, DNA with no drag-tag eluted as a single sharp peak with an electrophoretic mobility $\mu^o = 3.9 \times 10^4$ cm$^2$/V·s. Adding a 5- to 20-fold molar excess of the drag-tag to the DNA resulted in mixtures containing significant amounts of DNA with zero, one, or two drag-tags, as shown in FIG. 10B. Adding the drag-tag in a much larger molar excess (100-fold, relative to the DNA) led to nearly complete reaction of both ends of the DNA, again resulting in a single sharp peak as seen in FIG. 10C. Residual TCEP, present at 40-fold excess during the reduction, interferes somewhat with the reaction of the free thiols with the maleimide-activated drag-tags, and it was found that a significantly greater than 40-fold molar excess of drag-tag was necessary to achieve complete derivatization of both ends of the DNA. Species that were identified as ssDNA with one drag-tag typically appeared as a doublet of closely-spaced peaks, as with the middle peak in FIG. 10B. The reason for this was not immediately obvious, but one possibility is that slight differences in electrophoretic mobility arise from labeling at the 5'-end or 3'-end of the DNA molecule, since the thiol linkers at the two ends are of different lengths.

In the optimized protocol, excess maleimide was used to cap any remaining unreacted thiols. We did this because, in initial attempts to produce mixtures comprising significant amounts of DNA with zero or one drag-tag, additional peaks would appear at characteristic spots in the electropherogram, particularly between the peaks for DNA with one and two drag-tags, and trailing the peak for DNA with two drag-tags. The extra peaks would be absent when the samples were first analyzed, but would grow in magnitude over the course of hours to days after the reduction of the DNA and reaction with the drag-tags. Although the extra peaks were never conclusively identified, it was hypothesized that they resulted from re-oxidation of some of the residual free thiols to form disulfides. The addition of excess maleimide about two hours after the addition of the drag-tag effectively prevented this problem, as the maleimide rapidly reacts with any remaining free thiols. The capping of both ends of the dithiolated DNA with this small molecule was found to induce a small, almost negligible mobility shift of 2-3 seconds relative to reduced, uncapped dithiolated DNA, corresponding to an additional drag for the maleimide moiety equivalent to ~0.1 bases of DNA.

For each drag-tag (NMEG-20 or NMEG-40), samples consisting of both sizes of DNA (T20-dithiol or T40-dithiol) with zero, one, or two drag-tags were pooled to create mixtures containing multiple species, which were then separated and analyzed by CE. Run-to-run and capillary-to-capillary variabilities in migration time were generally quite low (approximately ±1%), allowing easy identification of peaks in the pooled samples by comparing to the migration times of the individual components prior to pooling. CE analyses of these pooled mixtures are shown in FIG. 11, along with the peak assignments. A simple visual inspection confirms the general predictions of the end-effects theory: 20mer DNA with two 20mer drag-tags (FIG. 11A, Peak 4) elutes later than 20mer DNA with one 40mer drag-tag (FIG. 11B, Peak 2), and likewise for the 40mer DNA (compare 11A, Peak 3 and FIG. 11B, Peak 1).

For the case of the migration of a DNA-drag-tag conjugate, with a charged DNA segment consisting of $M_C$ charged monomers, and an uncharged drag-tag consisting of $M_U$ uncharged monomers, the mobility $\mu$ is traditionally given by a weighted average of the electrophoretic mobilities of the charged and uncharged monomers:

$$\mu = \mu_0 \frac{M_C}{M_C + \alpha_1 M_U} \quad (2)$$

where $\mu_0$ is the mobility of the charged monomers (i.e. the free-solution mobility of DNA). (The uncharged monomers have zero electrophoretic mobility, and thus do not appear in the numerator of Equation (2)). The apparent overall frictional parameter $\alpha = \alpha_1 M_U$ (as given by Equation (2)) could be computed directly from the peak times in FIG. 11.

The $\alpha$ value calculated through use of Equation (2), which neglects the end-effect, is termed the "apparent" $\alpha$ value so as to distinguish it from that determined using other equations which account for the end-effect. The apparent $\alpha$ values, which qualitatively display the trend expected from the end-effects theory, are shown in Table 3.

TABLE 3

Apparent frictional parameter $\alpha$ for ssDNA with one or two drag-tags calculated from peak times in FIG. 11, with correction made for the slight mobility shift arising from the maleimide capping. The final column gives the ratio of the drag for a tag at each end versus the expected drag for a single tag of twice the size. Error margins on experimentally determined $\alpha$ values assume an uncertainty of ±0.05 minutes in peak times, which reflects the run-to-run and capillary-to-capillary variability observed with the instrument.

| DNA length | Drag-tag | Apparent $\alpha$ | Error (±) | Ratio [$\alpha_{(2)}$/ $2\alpha_{(1)}$] |
|---|---|---|---|---|
| 20 | NMEG-20 (one) | 5.1 | 0.07 | 1.07 |
|  | NMEG-20 (two) | 10.9 | 0.1 |  |
| 20 | NMEG-40 (one) | 9.7 | 0.1 | 1.09 |
|  | NMEG-40 (two) | 21.2 | 0.2 |  |
| 40 | NMEG-20 (one) | 6.1 | 0.08 | 1.06 |
|  | NMEG-20 (two) | 12.9 | 0.2 |  |
| 40 | NMEG-40 (one) | 11.2 | 0.2 | 1.09 |
|  | NMEG-40 (two) | 24.5 | 0.3 |  |

It is evident that two drag-tags give more than double the drag of a single tag, with roughly 6-9% enhancement for two drag-tags on ssDNA versus the expected drag for a single tag of twice the size. These experimental results will be analyzed quantitatively below, using the more detailed theory taking end-effects into account.

It is also clear from the results in Table 3 that the apparent $\alpha$ for a given size of drag-tag depends on the size of the DNA. For example, two NMEG-20 drag-tags on the 20mer DNA give $\alpha = 10.9$, whereas the same two NMEG-20 drag-tags on the 40mer DNA give $\alpha = 12.9$—a difference of 18%. This is in agreement with the end-effects theory: for a drag-tag of a fixed size on one or both ends, a longer DNA molecule means that the drag-tag monomers are relatively closer to the chain end (n/N closer to 0 and/or 1), thereby giving the drag-tag monomers a heavier weighting in determining the mobility of the conjugate. Thus, the apparent $\alpha$ value for a given drag-tag on one or both ends of the DNA increases as the DNA chain length increases.

Example 11

Analysis of dsDNA Conjugates

Double-stranded DNA conjugate molecules were produced by performing PCR using a thiolated forward primer and normal (unthiolated) reverse primer (for production of dsDNA conjugates with a drag-tag at one end only), Or using thiolated forward and reverse primers (for production of dsDNA conjugates with drag-tags at both ends). A large excess of TCEP was used for reduction of the thiols after the PCR reaction. Since TCEP is supplied as an HCl salt, the use of a large excess results in an acidification of the PCR buffer. To compensate for this, and to prevent long-term exposure of the DNA to very acidic conditions, additional 1 M Tris was added to the reduction mixture, resulting in a more acceptable pH. Following the reduction, the PCR products were purified using QIAquick spin columns, which effectively remove residual buffer salts, surfactants, enzyme, and reducing agents left over from the PCR reaction and reduction, which might otherwise interfere with reaction with the drag-tags.

The drag-tags used for the dsDNA conjugates were two moderately large synthetic polypeptoids (linear NMEG-44 and branched NMEG-70), and two protein polymers produced by genetic engineering of *E. coli*. The branched NMEG-70 and the P1-169 drag-tags have been described previously for the separation of denatured (single-stranded) PCR products of sizes similar to those described here [22, 24]. In this study, CE analysis was performed at room temperature with no denaturants in the buffer, ensuring that the DNA remained in its double-stranded state. Keeping the DNA in its double-stranded state allows for the easy incorporation of a drag-tag at both ends, which was expected to generate more than twice the drag of a single drag-tag, allowing the separation of a wider size range of dsDNA molecules.

The concentration of the DNA purified with the QIAgen spin column was too low for accurate measurement of absorbance at 260 nm, and thus the molar ratios of DNA to drag-tag are not known precisely. The amounts of drag-tag were generally sufficient to produce significant amounts of product with zero and one drag-tag (for products with only the forward primer thiolated), and zero, one, and two drag-tags (for PCR products with both primers thiolated). Typical electropherograms for two sizes of DNA (100 bp and 200 bp) with the P2-127 protein polymer are shown in FIG. 12. In each case, the "free" DNA (with no drag-tag) elutes around 6.2 minutes. In panels (A) and (C), which show PCR products generated with only a thiolated forward primer, the "free" DNA peak is followed by a single peak, corresponding to DNA with a single drag-tag. In panels (B) and (D), which show PCR products generated with both forward and reverse thiolated primers, there is an additional peak eluting 1-2 minutes later, corresponding to DNA with a drag-tag at both ends. Note also in panels (B) and (D) that, for the products generated with both primers thiolated, there are two closely spaced peaks eluting around the same time as the product with one drag-tag in panels (A) and (C). As with the split peaks for the ssDNA conjugates with one drag-tag, the exact cause of this phenomenon is unknown, but it was observed for all sizes of dsDNA with all of the drag-tags, and may result from slight differences in electrophoretic mobility arising from labeling at either end of the DNA molecules.

The P1-169 and P2-127 protein polymers used here as drag-tags were not entirely monodisperse [24], leading to some additional peak broadness. The additional broadness is most noticeable with the smaller sizes of DNA, and is more pronounced for the species with two drag-tags. Both of these effects are as expected. Sharper peaks for larger sizes of DNA conjugated to impure drag-tags (including P1-169) were reported in [24], and are also in line with theory presented in Reference [26]. The conjugation of a polydisperse drag-tag to both ends of a DNA molecule leads to a large number of possible combinations, earth with slightly different electrophoretic mobility, which is apparent as additional peak broadness. The NMEG-44 and branched NMEG-70 drag-tags, both of which were purified to near monodispersity by RP-HPLC, generate cleaner, sharper peaks than the protein polymer drag-tags.

Alpha values were calculated from the peak elution times of each species, and are plotted versus the DNA size $M_C$ in FIG. 13. In previous ELFSE literature, the relative mobilities of unlabeled and labeled DNA ($\mu_0/\mu$) would be plotted with respect to $1/M_C$, resulting in a straight line with slope $\alpha$ [1, 4]. This approach neglects the end-effects theory, which predicts a different overall value of $\alpha$ for each size of DNA. In this case, such plots are still essentially, linear (not shown), and can be used to give an average apparent value of $\alpha$ for each drag-tag. These average $\alpha$ values are given in Table 4, and are also drawn as horizontal lines in FIG. 13. (Note that the average a values determined by the linear fit of $\mu_0/\mu$ versus $1/M_C$ are not necessarily equal to the arithmetic average of the individual $\alpha$ values calculated for each size of DNA.) As indicated by the right-most ("Ratio") column in Table 4, the average $\alpha$ for two drag-tags is noticeably greater (10-23%) than twice $\alpha$ for a single-drag-tag, for these dsDNA species.

TABLE 4

Apparent frictional parameter α for dsDNA with one or two drag-tags, averaged for all sizes of DNA.
The final column gives the ratio of the drag for a tag at each end versus the expected drag for a single tag of twice the size.

| Drag-tag | Average α | Ratio [$\alpha_{(2)}/2\alpha_{(1)}$] |
|---|---|---|
| NMEG-44 (one) | 12.7 | 1.10 |
| NMEG-44 (two) | 28.0 | |
| Branched NMEG-70 (one) | 17.0 | 1.22 |
| Branched NMEG-70 (two) | 41.6 | |
| P1-169 (one) | 27.2 | 1.13 |
| P1-169 (two) | 61.7 | |
| P2-127 (one) | 19.9 | 1.23 |
| P2-127 (two) | 48.8 | |

Example 12

Discussion of Examples 6-11

The results obtained for the analysis of ssDNA conjugates with poly(NMEG) drag-tags can be compared directly to the predictions from the end-effect theory presented in Equations (4) and (6). To take the end-effect into account, the weighting function presented in Equation (5) is used. The parameter $\alpha_1$ for scaling the uncharged monomers can be calculated using the end-effect theory, but we must first account for the slight additional drag arising from the maleimide moiety added to cap any unreacted thiols. To find the drag $\alpha_m$ associated with a single malcimide cap, the following equation was solved (using Maple):

$$t = \frac{t_0(M_c + 2\alpha_m)}{\int_{\alpha_m}^{\alpha_m + M_c} \Psi\left(\frac{n}{M_c + 2\alpha_m}\right)dn} \quad (12)$$

where $t_0$ is the arrival time of the uncapped DNA, and t is the arrival time of the DNA capped on each end with maleimide. For the 20-base DNA, $\alpha_m$ was found to be 0.035, while for the 40-base DNA it was found to be 0.052. Since the end-effect theory was derived for long Gaussian chains, it is assumed that the $\alpha_m$ value found for the larger DNA chain more closely represents the true value.

Note that the fluorescein-dT base near the middle of the chain likely exerts some effect on the mobility, as the fluorescein carries a −2 charge, and the dye along with the spacer arm linking it to the dT base likely add some hydrodynamic friction. To properly account for this effect would require a dithiolated oligonucleotide with no fluorescein, which would be undetectable with the CE instrument used for the analysis. The effect of the fluorescein is likely moderated by its position near the middle of the DNA chain (and hence its lower weight in determining the electrophoretic mobility). Additionally, the experimental determinations of a were made by comparing mobilities of drab-tag-labeled and "free" DNA, all of which were labeled identically with fluorescein. The impact on the results is expected to be minimal, and thus the contributions of the fluorescein as well as the thiol linkers present on all of the DNA species are ignored.

For DNA with one drag-tag and one maleimide cap, $\alpha_1$ for the drag-tag can be found by solving Equation (13):

$$t_1 = \frac{t_0(M_c + \alpha_m + \alpha_1 M_u)}{\int_{\alpha_m}^{\alpha_m - M_c} \Psi\left(\frac{n}{M_c + \alpha_m + \alpha_1 M_u}\right) dn} \quad (13)$$

where $t_0$ is the arrival time of the DNA with no drag-tag (after correcting for the presence of maleimide caps on each end), and $t_1$ is the arrival time of the DNA with one maleimide cap and one drag-tag. The calculated values of $\alpha_1$ are presented in Table 5.

TABLE 5

Values of $\alpha_1$ for NMEG drag-tags calculated from experimental data for ssDNA, taking into account the theory of end-effects.

| DNA length ($M_C$) | Drag-tag length ($M_U$) | $\alpha_1$ |
|---|---|---|
| 20 | 20 | 0.19 |
|  | 40 | 0.21 |
| 40 | 20 | 0.20 |
|  | 40 | 0.21 |

Note that the closely spaced doublet for the arrival time of these singly labeled molecules was averaged for the results presented in Table 5; using either the faster or slower times resulted in $\alpha_1$ values that differed from the average by a negligible amount. Note that the values of $\alpha_1$ increase slightly with increasing size of the conjugate. For a given class of polymer, $\alpha_1$ is expected to be a constant that is related to the chemical structures of the components and the experimental conditions (i.e. monomer size and Kuhn length, ionic strength of the buffer). The slight variation among the conjugates is likely due to the fact that the DNA and the drag-tags are too small to be perfectly Gaussian in conformation, which is an underlying assumption for the theory of ELFSE. Since the largest molecules are expected to be the closest to being Gaussian in conformation, we use the corresponding value of $\alpha_1 = 0.21$ to represent the true value for the poly(NMEG) drag-tags under the current experimental conditions.

Using the end-effect theory, the predicted arrival time for DNA with two drag-tags is $$t_2 = \frac{t_0(M_c + 2\alpha_1 M_u)}{\int_{\alpha_1 M_u}^{\alpha_1 M_u + M_c} \Psi\left(\frac{n}{M_c + 2\alpha_1 M_u}\right) dn} \quad (14)$$

Equations (13) and (14) can now be used to predict the ratio of the mobilities of a bioconjugate with two drag-tags to the mobility of a conjugate with one drag-tag of twice the size, $\mu_2/\mu_1 = t_1/t_2$. The values predicted from Equations (13) and (14), using $\alpha_1 = 0.21$, are given in Table 6, along with the experimentally observed values, for the cases of 20mer or 40mer DNA with either a single 40mer drag-tag, or two 20mer drag-tags.

TABLE 6

Mobility ratio $\mu_2/\mu_1$ for two 20mer drag-tags ($\mu_2$) versus one 40mer drag-tag ($\mu_1$).

| DNA length ($M_C$) | Predicted $\mu_2/\mu_1$ | Experimental $\mu_2/\mu_1$ |
|---|---|---|
| 20 | 1.08 | 1.03 |
| 40 | 1.05 | 1.03 |

The experimental results are closer to the value of 1, which is that predicted by the simple theory in Equation (2) that neglects end-effects. The experimental value for the 40mer DNA is closer to the values predicted by the end-effect theory; this may be because the larger chains more closely approximate Gaussian coils, and are thus more appropriate test cases for the theory.

The quantitative end-effect theory is not directly applicable to the dsDNA data presented here. Although the dsDNA products are significantly longer, dsDNA is also considerably stiffer, with a much longer persistence length than ssDNA. Thus, even the longer dsDNA products are more likely to resemble stiff rods or cylinders, rather than random coils. Even with such a geometry, there is still likely an end-effect, which is dramatically illustrated by the experimental measurements of a presented in Table 4. Since the dsDNA-drag-tag conjugates are not likely to even approximate Gaussian coils, application of the theory used for the ssDNA conjugates is not appropriate.

The drag enhancement for placing a drag-tag at each end of dsDNA is noticeably larger than was observed for placing a drag-tag at each end of ssDNA. This could simply be a function of the specific sizes of DNA and drag-tags that were chosen for study, but it may also be the result of the stiff rod-like structure of the dsDNA. Because the dsDNA molecules studied here are relatively short, the ends of the dsDNA molecule are more often on the "outside" of the chain, as opposed to a true Gaussian coil for which the chain ends may occupy positions in the interior of the coil. In addition, there may be a greater degree of hydrodynamic segregation between the rod-like dsDNA and the random coil drag-tags. Detailed theoretical analysis is required to determine if these simple arguments can explain the larger end-effect observed for dsDNA in these experiments.

The enhanced drag arising from placing a drag-tag at both ends of DNA leads to interesting new possibilities for sequencing and genotyping by ELFSE. The separation capacity of ELFSE is tied directly to the amount of friction generated by the drag-tag, and previous efforts have been focused on creating larger drag-tags to generate more friction. The possibility of including a drag-tag at both ends extends the range of separations that are possible with existing drag-tags. This is particularly important as the production of very large, totally monodisperse protein polymer drag-tags has proven difficult [15, 24].

This application has provided verification of an important and interesting prediction of the new theory of end-effects in ELFSE separations. Using both custom-synthesized ssDNA oligonucleotides and larger dsDNA products generated by PCR, labeled at one or both ends with a variety of drag-tags, it has been shown that the drag induced by labeling both ends is more than double the drag arising from a single drag-tag at one end, and is also larger than the drag that would arise from a single drag-tag of twice the size at one end. The effect is significant, with drag ($\alpha$) enhanced by 6-9% for the ssDNA and by 10-23% for the dsDNA in the size range tested with the available drag-tags. This enhanced drag from double end-labeling is useful for various types of ELFSE separations such as DNA sequencing, which will require incorporation of a drag-tag on each end of the ssDNA prior to analysis.

Example 13

Review of Preferred Methods of the Invention

For greater clarity, two preferred methods of the invention are reviewed with reference to FIGS. 14 and 15.

FIG. 14 illustrates a method in which polymeric compounds are provided. In step 100 the polymeric compounds are modified by attaching a chemical moiety at or near each end of the polymeric compounds to generate doubly end labeled polymeric compounds. In step 101 the double end labeled polymeric compounds are subjected to free-solution electrophoresis, thereby to cause separation thereof.

FIG. 15 illustrates a method for DNA sequencing, which involves in step 200 synthesizing a plurality of ssDNA molecules each comprising a sequence identical to at least a portion of a section of DNA, each ssDNA having a length corresponding to a position of a specific nucleotide in the sequence of the section of DNA. Subsequently, the ssDNAs are modified in step 201 to attach a chemical moiety at or near each end thereof. The doubly end labeled ssDNAs san then be subjected in step 202 to free-solution electrophoresis, thereby to cause separation thereof. In step 203 the nucleotide sequence can be identified by comparing the relative mobility of the doubly end labeled DNAs.

While the invention has been described with reference to particular preferred embodiments thereof, it will be apparent to those skilled in the art upon a reading and understanding of the foregoing that numerous methods for polymeric compound modification and separation other than the specific embodiments illustrated are attainable, which nonetheless lie within the spirit and scope of the present invention. It is intended to include all such designs, assemblies, assembly methods, and equivalents thereof within the scope of the appended claims.

REFERENCES

[1] Ren, H., Karger, A. E., Oaks, F., Menchen, S., Slater, G. W., Drouin, G., *Electrophoresis* 1999, 20, 2501-2509.

[2] Völkel, A. R., Noolandi, J., *Macromolecules* 1995, 28, 8182-8189.

[3] Mayer, P., Slater, G. W., Drouin, G., *Anal. Chem.* 1994, 66, 1777-1780.

[4] Heller, C., Slater, G. W., Mayer, P., Dovichi, N., Pinto, D., Viovy, J.-L., Drouin, G., *J. Chrom. A.* 1998, 806, 113-121.

[5] Desruisseaux, C., Long, D., Drouin, G., Slater, G. W., *Macromolecules* 2001, 34, 44-52.

[6] Desruisseaux, C., Drouin, G., Slater, G. W., *Macromolecules* 2001, 34, 5280-5286.

[7] Viovy, J. L., *Rev. Mod. Phys.* 2000, 72, 813-872.

[8] Olivera, B. M., Baine, P., Davidson, N., *Biopolymers* 1964, 2, 245-257.

[9] Stellwagen, N. C., Gelfi, C., Righetti, P. G., *Biopolymers* 1997, 42, 687-703.

[10] Stellwagen, N. C., Stellwagen, E., *Electrophoresis* 2002, 23, 1935-1941.

[11] Vreeland, W. N., Desruisseaux, C., Karger, A. B., Drouin, G., Slater, G. W., Barron, A. E., *Anal. Chem.* 2001, 73, 1795-1803.

[12] Vreeland, W. N., Slater, G. W., Barron, A. E., *Bioconj. Chem.* 2002, 13, 663-670.

[13] McCormick, L. C., Slater, G. W., Karger, A. E., Vreeland, W. N., Barron, A. E., Desruisseaux, C., Drouin, G., *Electrophoresis* 2001, 924, 43-52.

[14] Long, D., Dobrynin, A. V., Rubinstein, M., Ajdai, A., *J. Chem. Phys.* 1998, 108, 1234-1244.

[15] Won, J.-I., Meagher, R. J., Barron, A. E., *Biomacromolecules* 2004, 5, 618-627.

[16] Noolandi, J., "A New Concept For Sequencing DNA By Capillary Electrophoresis", *Electrophoresis* 1992, 13, 394-395.

[17] Meagher, R. J., Won, J. I., McCormick, L. C., Nedelcu, S., Bertrand, M. M., et al., "End-labeled free-solution electrophoresis of DNA.", *Electrophoresis* 2005, 26, 331-350.

[18] Bullock, J., *J. Chrom.* 1993, 645, 169-177.

[19] Zuckermann, R. N., Kerr, J. M., Kent, S. B. H., Moos, W. H., "Efficient Method For the Preparation of Peptoids [Oligo(N-Substituted Glycines)] By Submonomer Solid-Phase Synthesis", *J. Am. Chem. Soc.* 1992, 114, 10646-10647.

[20] Vreeland, W. N., Barron, A. E., "Free-solution capillary electrophoresis of polypeptoid-oligonucleotide conjugates", *Abstracts of Papers of the American Chemical Society* 2000, 219, 555-556.

[21] Vreeland, W. N., Meagher, R. I., Barron, A. E., "Multiplexed, High-Throughput Genotyping by Single-Base Extension and End-Labeled Free-Solution Electrophoresis", *Anal. Chem.* 2002, 74, 4328-4333.

[22] Haynes, R. D., Meagher, R. J., Won, J. I., Bogdan, F. M., Barron, A. E., "Comb-like, monodisperse polypeptoid drag-tags for DNA separation by End-Labeled Free-Solution Electrophoresis (ELFSE)", *Bioconjugate Chem.* 2005, 16, 929-938.

[23] Won, J. I., Barron, A. E., "A new cloning method for preparation of long repetitive polypeptides without sequence requirement", *Macromolecules* 2002, 35, 8281-8287.

[24] Won, J. I., Meagher, R. J., Barron, A. E., "Protein polymer drag-tags for DNA separations by end-labeled free-solution electrophoresis;", *Electrophoresis* 2005, 26, 2138-2148.

[25] Doherty, E. A. S., Berglund, K. D., Buchholz, S. A., Kourkine, I. V., Przybycien, T. M., et al., "Critical factors for high-performance physically adsorbed (dynamic) polymeric wall coatings for capillary electrophoresis of DNA", *Electrophoresis* 2002, 23, 2766-2776.

[26] McCormick, L. C., Slater, G. W., Karger, A. E., Vreeland, W. N., Barron, A. E., et al., "Capillary electrophoretic separation of uncharged polymers using polyelectrolyte engines—Theoretical model", *J. Chromatogr. A* 2001, 924, 43-52.

The invention claimed is:

1. A method for separating single-stranded polymeric compounds according to their relative molecular lengths, the method comprising:
   attaching a chemical moiety at or near each end of each of said single-stranded polymeric compounds to generate doubly end-labeled polymeric compounds; and
   subjecting the doubly end-labeled polymeric compounds to free-solution electrophoresis, each chemical moiety suitable to impart increased hydrodynamic friction to each end of each doubly end-labeled polymeric compound thereby to facilitate separation of the doubly end-labeled polymeric compounds according to their electrophoretic mobilities during said free-solution electrophoresis.

2. The method of claim 1, wherein the single-stranded polymeric compounds to be separated are linear polymeric compounds.

3. The method of claim 1, wherein the single-stranded polymeric compounds to be separated are charged polymeric compounds.

4. The method of claim 1, wherein the chemical moieties attached as end-labels are uncharged or substantially uncharged chemical moieties.

5. The method of claim 1, wherein the single-stranded polymeric compounds to be separated are selected from among polypeptides or polynucleotides.

6. The method of claim 5, wherein the single-stranded polymeric compounds to be separated are selected from among the polynucleotides, including single-stranded DNA, and RNA.

7. The method of claim 1, wherein the chemical moieties attached as end-labels are selected from polypeptides, polypeptoids, and polypeptide-polypeptoid conjugates.

8. The method according to claim 1, wherein the chemical moieties are selected from the group consisting of Streptavidin, or a derivative thereof, N-methoxyethylglycine (NMEG)-based polymers of length up to 3100 monomer units, and a molecule consisting of a poly(NMEG) backbone optionally grafted with oligo (NMEG) branches.

9. A method for sequencing a section of a DNA molecule the method comprising:
   (a) synthesizing a first plurality of ssDNA molecules each comprising a sequence identical to at least a portion at or near the 5' end of slid section of DNA, said ssDNA molecules having substantially identical 5' ends but having variable lengths, the length of each ssDNA molecule corresponding to a specific adenine base in said section of DNA;
   (b) synthesizing a second plurality of ssDNA molecules each comprising a sequence identical to at least a portion at or near the 5' end of said section of DNA, said ssDNA molecules having substantially identical 5' ends but having variable lengths, the length of each ssDNA molecule corresponding to a specific cytosine base in said section of DNA;
   (c) synthesizing a third plurality of ssDNA molecules each comprising a sequence identical to at least a portion at or near the 5' end of said section of DNA, said ssDNA molecules having substantially identical 5' ends but having variable lengths, the length of each ssDNA molecule corresponding to a specific guanine base in said section of DNA;
   (d) synthesizing a fourth plurality of ssDNA molecules each comprising a sequence identical to at least a portion at or near the 5' end of aid section of DNA, said ssDNA molecules having substantially identical 5' ends but having variable lengths, the length of each ssDNA molecule corresponding to a specific thymine base in said section of DNA;
   (e) attaching a chemical moiety to end nucleotides at or near each end of said ssDNA molecules to generate doubly end-labeled polymeric compounds; and
   (f) subjecting each plurality of ssDNA molecules to free-solution electrophoresis; and
   (g) identifying the nucleotide sequence of the section of DNA in accordance with the relative electrophoretic mobilities of the ssDNAs in each plurality of ssDNAs;
   wherein any of steps (a), (b), (c), and (d) may be performed in any order or simultaneously; and whereby each chemical moiety imparts increased hydrodynamic friction to each end of each doubly end-labeled polymeric compound thereby to facilitate separation of the doubly end-labeled polymeric compounds according to their electrophoretic mobility.

10. The method of claim 9, wherein the chemical moieties are uncharged chemical moieties.

11. The method of claim 9, wherein the chemical moieties are selected from among polypeptides and polypeptoids.

12. The method of claim 9, wherein the chemical moieties are selected from the group consisting of Streptavidin, or a derivative thereof, N-methoxyethylglycine (NMEG) based polymers comprising up to 300 monomer units, and a molecule consisting of a poly(NMEG) backbone optionally grafted with oligo (NMEG) branches.

13. The method according to claim 9, wherein the section of DNA comprises less than 2000 nucleotides.

14. The method according to claim 13, wherein the section of DNA comprises less than 1000 nucleotides.

15. The method according to claim 14, wherein the section of DNA comprises less than 500 nucleotides.

16. The method according to claim 15, wherein the section of DNA comprises less than 300 nucleotides.

17. The method according to claim 16, wherein the section of DNA comprises less than 100 nucleotides.

18. A method for separating single-stranded polymeric compounds differentiated in size by at least one polymer unit, the method comprising:

attaching a chemical moiety at or near each end of the single-stranded polymeric compounds; and subjecting the single-stranded polymeric compounds with the attached chemical moieties to free-solution electrophoresis, each chemical moiety imparting increased hydrodynamic friction to each end of said polymeric compounds to thereby modify the electrophoretic mobility of said single-stranded polymeric compounds.

19. The method of claim 18, wherein the difference in relative size of the single-stranded polymeric compounds is a single polymer unit.

20. The method of claim 19, wherein the single-stranded polymeric compounds comprise single-stranded DNA molecules, and each polymer unit is a nucleotide.

* * * * *